United States Patent
Bajpai et al.

(10) Patent No.: US 11,127,488 B1
(45) Date of Patent: Sep. 21, 2021

(54) MACHINE LEARNING SYSTEMS FOR AUTOMATED PHARMACEUTICAL MOLECULE SCREENING AND SCORING

(71) Applicant: Accenture Global Solutions Limited, Dublin (IE)

(72) Inventors: Dhruv Bajpai, Bangalore (IN); Praveen Viswanathan, Jodhpur (IN); Ashish Ambasta, Bangalore (IN); Vighnesh Paramasivam, Coimbatore (IN)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 17/155,021

(22) Filed: Jan. 21, 2021

(30) Foreign Application Priority Data

Sep. 25, 2020 (IN) .............................. 202041041670

(51) Int. Cl.
*G16C 20/50* (2019.01)
*G16C 20/70* (2019.01)

(52) U.S. Cl.
CPC .............. *G16C 20/50* (2019.02); *G16C 20/70* (2019.02)

(58) Field of Classification Search
CPC ................................ G16C 20/50; G16C 20/70
USPC .......................................................... 706/11
See application file for complete search history.

(56) References Cited

U.S. PATENT DOCUMENTS

| | | |
|---|---|---|
| 6,813,615 B1 | 11/2004 | Colasanti et al. |
| 2017/0161635 A1 | 6/2017 | Oono et al. |
| 2020/0303041 A1 | 9/2020 | Narayanan et al. |
| 2020/0372369 A1 | 11/2020 | Gong et al. |
| 2020/0388401 A1 | 12/2020 | Spiro et al. |
| 2021/0065913 A1 | 3/2021 | Yuan et al. |
| 2021/0081804 A1 | 3/2021 | Stojevic et al. |

*Primary Examiner* — Jerry Lin
(74) *Attorney, Agent, or Firm* — Norton Rose Fulbright US LLP

(57) ABSTRACT

Aspects of the present disclosure provide systems, methods, and computer-readable storage media that leverage artificial intelligence and machine learning to screen candidate pharmaceutical molecules or compounds for pharmaceutical uses (e.g., treating diseases or conditions). The screening may be based on structural similarity between the candidate pharmaceutical molecules and various pharmaceutical targets (e.g., proteins, nucleic acids, etc.). In aspects, one or more machine learning (ML) models may be trained to assign a candidate pharmaceutical molecule to one of multiple clusters based on chemical/physical properties of the candidate pharmaceutical molecule and chemical/physical properties of pharmaceutical targets associated with the clusters. The pharmaceutical targets associated with the cluster may be scored based on comparisons between the candidate pharmaceutical molecule and the pharmaceutical target, and a subset of the pharmaceutical targets may be identified based on the scores. In some implementations, the subset may be ranked using conjoint analysis and machine learning.

20 Claims, 4 Drawing Sheets

MACHINE LEARNING SYSTEMS FOR AUTOMATED PHARMACEUTICAL MOLECULE SCREENING AND SCORING

CROSS-REFERENCE TO RELATED APPLICATIONS

The present application claims priority to Indian Provisional Patent Application No. 202041041670, filed on Sep. 25, 2020, entitled "DRUG DISCOVERY AND SEARCH USING MACHINE LEARNING," and the present application is related to co-pending U.S. patent application Ser. No. 17/154,417, entitled "MACHINE LEARNING SYSTEMS FOR AUTOMATED PHARMACEUTICAL MOLECULE IDENTIFICATION," filed Jan. 20, 2021, the contents of each of which are expressly incorporated herein in their entirety.

TECHNICAL FIELD

The present disclosure relates to systems and methods for leveraging machine learning and artificial intelligence to automatically screen candidate pharmaceutical molecules and compounds for use in treating target diseases or conditions and to score the candidate pharmaceutical molecules.

BACKGROUND

Pharmaceuticals are one of the largest and most profitable industries in the world, as illustrated by the worldwide pharmaceutical market being worth approximately 1.3 trillion dollars in 2019 according to some estimates. In addition to researching and manufacturing new drugs (e.g., pharmaceuticals) to cure or treat new diseases or conditions, pharmaceutical companies spend significant resources researching and "discovering" (e.g., identifying) new drugs for known diseases that have increased efficacy, fewer side effects, and fewer harmful drug interactions. For example, a pharmaceutical company may try to optimize and improve an already manufactured drug for a specific disease with the goal of improving efficacy and reducing side effects.

Designing (e.g., discovering or identifying) new drugs is typically a manually-intensive process. To design a new drug for a particular disease, a human drug expert (e.g., a chemist, biochemist, researcher, etc.) may consider a known molecule or compound used in a currently-available drug for treating the particular disease, and the human drug expert may identify multiple candidate molecules based on the known molecule. For example, the human drug expert may decide to add an additional element to, remove an element from, or modify the physiochemical structure of, the known molecule or compound based on their experience and knowledge to design candidate molecules. The candidate molecules may be visually screened by the human drug expert, and a selected subset of candidate molecules that pass the visual screening may be further screened using lab experiments or other testing. Thus, the drug design (also referred to as drug discovery or drug identification) process is limited by the knowledge and experience of the human drug expert. Additionally, the human drug expert may focus their attention on the particular disease to be treated, which may result in the human drug expert failing to explore or consider molecules or compounds that are not widely known as useful in treating the particular disease, which may limit the search space for the candidate molecules.

Conventional drug discovery may be a long and expensive process. For example, each new drug, from discovery to launch, typically takes approximately twelve to fifteen years and cost approximately 1.2 billion dollars. Additionally, the drug discovery process includes many different steps such as discovery, optimization, preclinical trials, phased clinical trials, registration, and eventual launch. During many or all of these steps, a significant portion of the candidate molecules or compounds are filtered out or otherwise rejected. For example, by some estimations, only approximately 1.8% of newly identified molecules or compounds are successfully tested and implemented into pharmaceuticals released to consumers.

Another part of the drug discovery process that can take considerable time and resources is the screening process. The screening may include evaluating whether candidate molecules or compounds are likely to bind to "pharmaceutical targets," also referred to as "drug targets," such as proteins (e.g., structural proteins, enzymes, ion channels, receptors (e.g., G protein-coupled receptors, nuclear hormone receptors), membranes, etc.), nucleic acids (e.g., DNA, RNA, etc.), cells, or the like, and evaluating which pharmaceutical targets are the most likely to bind to particular candidate molecules or compounds. For example, a human drug expert may compare a molecular fingerprint or structure of a candidate molecule to molecular fingerprints or structures of particular pharmaceutical targets to determine whether the candidate molecule is likely to bind to the particular pharmaceutical targets, and thus is likely to treat a particular disease or condition associated with the particular pharmaceutical targets. Because the chemical search space (e.g., the total number of candidate molecules or compounds and pharmaceutical targets available for screening) is approximately $10^{60}$, screening large quantities of candidate molecules or compounds against large quantities of pharmaceutical targets becomes an intractable problem. Thus, the screening process typically involves only a limited number of candidate molecules or compounds, or a limited number of pharmaceutical targets, which may limit the success of the screening process or the utility of the selected molecules or compounds. Increasing the number of candidate molecules or compounds, or pharmaceutical targets, that are considered may significantly increase the time and resource cost associated with the screening process. Additionally, once candidate molecules or compounds that satisfy the screening process are identified, it can be time and resource intensive to predict which candidate molecules or compounds will form the most commercially successful, or otherwise desirable, drugs. For example, there may not be a one-to-one correspondence between chemical properties and desired drug properties, such as efficacy, side effects, solubility, and the like, or commercial success. Additionally, typical ranking techniques involve significant input information from a client, customers, news sources, and the like, as well as analysis of the input information by human analysts, which can further increase the time and resource cost of the drug discovery process.

SUMMARY

Aspects of the present disclosure provide systems, methods, and computer-readable storage media for automated screening of candidate pharmaceutical molecules or compounds for use in treating target diseases or conditions, such as by identifying uses of new molecules or compounds or identifying new uses of existing molecules or compounds. The screening process may also be referred to as searching for pharmaceutical targets (e.g., drug targets) that are sufficiently similar to the candidate pharmaceutical molecules or compounds. In some aspects, the screening (e.g., searching) process may include identifying one or more pharmaceutical targets having chemical or physical properties that are sufficiently similar to chemical or physical properties of the candidate pharmaceutical molecules such that the candidate pharmaceutical molecules will (or are likely to) bind (e.g., covalent binding and/or non-covalent binding (e.g., electrostatic interactions, hydrogen bonds, van der Waals interactions, hydrophobic interactions, ion induced dipole interaction, dipole induced dipole interaction, etc.) with the pharmaceutical targets. If a candidate molecule binds with a pharmaceutical target, the candidate molecule may modify the activity of the pharmaceutical target to cause a particular effect, such as a therapeutic effect related to a particular disease state or condition. For example, the pharmaceutical targets may include proteins (e.g., structural proteins, enzymes, ion channels, receptors (e.g., G protein-coupled receptors, nuclear hormone receptors), membranes, etc.), nucleic acids (e.g., DNA, RNA, etc.), cells, and the like, and by binding with the proteins, nucleic acids, cells, or other pharmaceutical targets, a candidate molecule may prevent the protein, nucleic acid, cell, etc., from binding to other endogenous substances or stimulate a change in a function (e.g., upregulate, downregulate, inhibit, etc.) of the protein, nucleic acid, cell, etc.

To facilitate automated screening of candidate pharmaceutical molecules or compounds, a drug discovery or screening platform may train and leverage artificial intelligence and machine learning based on binding data acquired from a variety of sources, such as publically available binding information databases, third party binding information databases, proprietary databases, and the like. The binding data may indicate chemical properties of multiple different pharmaceutical targets, such as physiochemical structures of the pharmaceutical targets, molecular shapes of the pharmaceutical targets, molecular fingerprints of the pharmaceutical targets, and the like. The binding data may be processed and transformed into a form that may be used as training data. For example, if the binding data includes simplified molecular-input line-entry system (SMILES)-formatted data that represents molecular structure as a string of letters and characters, natural language processing may be performed on the SMILES-formatted data to convert the strings to numerical data for vectorization into training data. Such training data may be used to train the artificial intelligence or machine learning to group the pharmaceutical targets into multiple clusters associated with similar chemical properties (e.g., molecular structures, shapes, fingerprints, and the like).

To screen a candidate pharmaceutical molecule (or compound), the candidate pharmaceutical molecule may be assigned to a cluster by the trained artificial intelligence and machine learning, and the pharmaceutical targets that are members of the cluster may be compared to the candidate pharmaceutical molecule for scoring to filter the pharmaceutical targets to a high-scoring subset. The candidate pharmaceutical molecule or compound may be a previously-identified pharmaceutical molecule or compound, such as a previously-identified pharmaceutical molecule or compound that is included in a database of pharmaceutical information (e.g., the Zinc database, as a non-limiting example), or a pharmaceutical molecule that is identified using trained generative machine learning, as further described herein. Thus, previously-identified pharmaceutical molecules or compounds may be screened to identify new uses (e.g., to identify previously-uncontemplated pharmaceutical targets to bind with, thereby indicating usefulness in treating additional disease states or conditions than previously known), and newly-identified pharmaceutical molecules or compounds may be screened to identify their uses (e.g., to identify a pharmaceutical target for binding to treat a corresponding disease or condition). In some implementations, the subset of pharmaceutical targets may then be automatically ranked based on conjoint analysis using additional artificial intelligence and machine learning.

In aspects, a computing device (e.g., a server or other device that implements a drug discovery or screening platform) may acquire binding data from one or more databases, such as the publically available BindingDB database, DrugBank database, Therapeutic Targets Database, Zinc database ("Zinc15" or "Zinc12"), and SIDER database ("SIDER Side Effects Resource"), as non-limiting examples. The binding data may indicate chemical properties (e.g., physiochemical structures, molecular shapes, molecular fingerprints, etc.) associated with multiple pharmaceutical targets. The computing device may convert at least a portion of the binding data to training data. For example, the computing device may perform natural language processing on text data or SMILES-formatted data to convert the text data or SMILES-formatted data into extracted features. The extracted features may be vectorized or otherwise grouped to generate the training data. In some implementations, the computing device may perform pre-processing, such as filtering, outlier removal, filling in missing entries, dimensionality reduction, or the like on the binding data prior to converting the binding data to the training data.

After generating the training data, the computing system may train one or more machine learning models based on the training data. Such training may configure the machine learning models to group molecules into clusters based on chemical properties of the molecules. For example, the machine learning models may group the pharmaceutical targets into multiple clusters such that members of each cluster have similar chemical properties. In some implementations, the machine learning models may be configured to perform sparse subspace clustering to group the molecules into clusters. After training the machine learning models, the computing device may use the machine learning models to assign a candidate pharmaceutical molecule or compound to one of the clusters based on chemical properties of the candidate pharmaceutical molecule. Members (e.g., multiple pharmaceutical targets) of the cluster to which the candidate pharmaceutical molecule is assigned may be scored based on comparisons between the pharmaceutical targets and the candidate pharmaceutical molecule, and a subset of the pharmaceutical targets may be selected based on the scores. In some implementations, for each pharmaceutical target that is a member of the cluster, comparisons between molecular fingerprints of the pharmaceutical target and molecular fingerprints of the candidate pharmaceutical molecule may be performed to generate multiple similarity scores, such as a Tanimoto coefficient, a cosine similarity, a largest common string (LCS) similarity, a Library for the Enumeration of Modular Natural Structures (LEMONS)-based similarity, a retrobiosynthesis and alignment (GRAPE) similarity, and the like, and a composite score for the pharmaceutical target is generated by averaging the multiple similarity scores. In such implementations, pharmaceutical targets having composite scores that satisfy one or more thresholds may be selected as the subset of pharmaceutical targets. In some implementations, the subset of pharmaceutical targets may be ranked using conjoint analysis and additional machine learning models to indicate the predicted commercial success, or another metric, of drugs formed by the candidate pharmaceutical molecule and the respective pharmaceutical target.

The computing device may generate an output that indicates the candidate pharmaceutical molecule and one or more of the subset of pharmaceutical targets for testing and potential trial. For example, the computing device may initiate display of a graphical user interface (GUI) that includes text, images, graphics, or a combination thereof, that indicate the candidate pharmaceutical molecule and the pharmaceutical targets, such as molecule names, names of elements that make up the molecules, two-dimensional graphical representations of the molecules, SMILES representations of the molecules, predicted properties of the molecules, disease states or conditions that are predicted to be treated using the molecules, and the like. Additionally or alternatively, the computing device may provide instructions to a drug production system to initiate generation of samples of drugs that combine the candidate pharmaceutical molecule and the pharmaceutical targets. In some implementations, the computing device may operate as a training device that trains the machine learning models and provides the machine learning models (or data indicative of the configuration of the machine learning models) to client devices for pharmaceutical molecule screening at the client devices.

The present disclosure describes systems that provide improvements compared to other drug screening systems. For example, the present disclosure describes systems that may train machine learning models to automatically identify a group of pharmaceutical targets that are at least somewhat chemically or structurally related to a candidate pharmaceutical molecule or compound (e.g., via clustering of pharmaceutical targets based on chemical properties or structural properties). In some implementations, the clustering may include density-based spatial clustering of applications with noise (DBSCAN), K-means clustering, K-means for large-scale clustering (LSC-K), longest common subsequence (LCS) clustering, longest common cyclic subsequence (LCCS) clustering, or the like. Identifying a group of pharmaceutical targets that are more likely to bind to the candidate pharmaceutical molecule or compound from a much larger group of pharmaceutical targets limits the search space for screening the candidate pharmaceutical molecule or compound, which may enable scoring, filtering, and identification of a selected subset of pharmaceutical targets faster, and using less processing resources, than systems that implement "brute force" techniques to analyze and score an entirety of the larger group of pharmaceutical targets. Additionally or alternatively, the machine learning models may be trained using a large amount of binding data as training data, which enables the machine learning models to learn underlying relationships between chemical or physical properties of pharmaceutical targets that would not be apparent to human drug experts due to their limited experience and knowledge, or their focus on finding a relationship with a particular pharmaceutical target for treating a particular disease or condition. Automatically ranking the selected subset of pharmaceutical targets may also reduce the cycle time and cost associated with selecting the most commercially successful drugs to test. By screening candidate pharmaceutical molecules or compounds against pharmaceutical targets in a shorter period of time and using fewer resources, the systems and methods described herein may substantially reduce the costs and shorten the development cycle associated with discovering and launching new drugs (e.g., pharmaceuticals) or discovering new pharmaceutical uses for existing drugs, pharmaceutical molecules, or compounds. The drug, pharmaceutical molecule, or compound may include, but is not limited to, small molecule drugs and biologics.

In a particular aspect, a method for pharmaceutical molecule screening using machine learning includes providing, by one or more processors, input data indicating a candidate pharmaceutical molecule to one or more machine learning (ML) models to identify a cluster of multiple clusters to which the candidate pharmaceutical molecule is assigned. The one or more ML models are configured to assign molecules to one of the multiple clusters based on chemical or physical properties of the molecules. Each cluster of the multiple clusters is associated with a respective plurality of pharmaceutical targets assigned to the cluster based on chemical or physical properties of the respective plurality of pharmaceutical targets. The method also includes, for each pharmaceutical target of a plurality of pharmaceutical targets associated with the cluster, determining, by the one or more processors, a respective composite score based on one or more comparisons between the candidate pharmaceutical molecule and the pharmaceutical target. The method includes identifying, by the one or more processors, a subset of pharmaceutical targets from the plurality of pharmaceutical targets associated with the cluster based on the composite scores. The method further includes generating, by the one or more processors, an output based on the subset of pharmaceutical targets and the candidate pharmaceutical molecule.

In another particular aspect, a system for pharmaceutical molecule screening using machine learning includes a memory and one or more processors communicatively coupled to the memory. The one or more processors are configured to provide input data indicating a candidate pharmaceutical molecule to one or more ML models to identify a cluster of multiple clusters to which the candidate pharmaceutical molecule is assigned. The one or more ML models are configured to assign molecules to one of the multiple clusters based on chemical or physical properties of the molecules. Each cluster of the multiple clusters is associated with a respective plurality of pharmaceutical targets assigned to the cluster based on chemical or physical properties of the respective plurality of pharmaceutical targets. The one or more processors are also configured to determine, for each pharmaceutical target of a plurality of pharmaceutical targets associated with the cluster, a respective composite score based on one or more comparisons between the candidate pharmaceutical molecule and the pharmaceutical target. The one or more processors are configured to identify a subset of pharmaceutical targets from the plurality of pharmaceutical targets associated with the cluster based on the composite scores. The one or more processors are further configured to generate an output based on the subset of pharmaceutical targets and the candidate pharmaceutical molecule.

In another particular aspect, a non-transitory computer-readable storage medium stores instructions that, when executed by one or more processors, cause the one or more processors to perform operations for pharmaceutical molecule screening using machine learning. The operations include providing input data indicating a candidate pharmaceutical molecule to one or more ML models to identify a cluster of multiple clusters to which the candidate pharmaceutical molecule is assigned. The one or more ML models are configured to assign molecules to one of the multiple clusters based on chemical or physical properties of the molecules. Each cluster of the multiple clusters is associated with a respective plurality of pharmaceutical targets assigned to the cluster based on chemical or physical properties of the respective plurality of pharmaceutical targets. The operations also include for each pharmaceutical target of a plurality of pharmaceutical targets associated with the cluster, determining a respective composite score based on one or more comparisons between the candidate pharmaceutical molecule and the pharmaceutical target. The operations include identifying a subset of pharmaceutical targets from the plurality of pharmaceutical targets associated with the cluster based on the composite scores. The operations further include generating an output based on the subset of pharmaceutical targets and the candidate pharmaceutical molecule.

In the context of the present disclosure the terms "molecule" and "compound" can be used interchangeably. Non-limiting examples of molecules and compounds can include small molecules and biologics. In one non-limiting aspect, small molecules can be chemically derived such as by being manufactured through chemical synthesis or isolated from another material having the small molecule. In one non-limiting aspect, biologics can include a material or substance extracted from, synthesized by, or manufactured from living organisms (e.g., microorganisms, plants, animals, cells, etc.). Non-limiting examples of biologics can include sugars, polymers, peptides, proteins, enzymes, or nucleic acids or combinations thereof. In some particular instances, the biologic can be a monoclonal or polyclonal antibody or antibody fragment thereof. In the context of the present disclosure the terms "pharmaceutical target" and "drug target" can be used interchangeably. Pharmaceutical targets and drug targets can refer to native materials or substances in a body of a living organism whose activity may be modified by a pharmaceutical molecule (e.g., of a drug or other pharmaceutical product) by physically binding (e.g., covalent or non-covalent bond formation) with the pharmaceutical molecule. Non-limiting examples of pharmaceutical targets and drug targets may include proteins and nucleic acids. Non-limiting examples of such proteins may include protein receptors, enzymes (e.g., protein kinases, proteases, esterases, phosphatases, etc.), ion channels, nuclear hormone receptors, structural proteins, and membrane transport proteins.

The foregoing has outlined rather broadly the features and technical advantages of the present disclosure in order that the detailed description that follows may be better understood. Additional features and advantages will be described hereinafter which form the subject of the claims of the disclosure. It should be appreciated by those skilled in the art that the conception and specific aspects disclosed may be readily utilized as a basis for modifying or designing other structures for carrying out the same purposes of the present disclosure. It should also be realized by those skilled in the art that such equivalent constructions do not depart from the scope of the disclosure as set forth in the appended claims. The novel features which are disclosed herein, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present invention, reference is now made to the following descriptions taken in conjunction with the accompanying drawing, in which.

Figure 1:
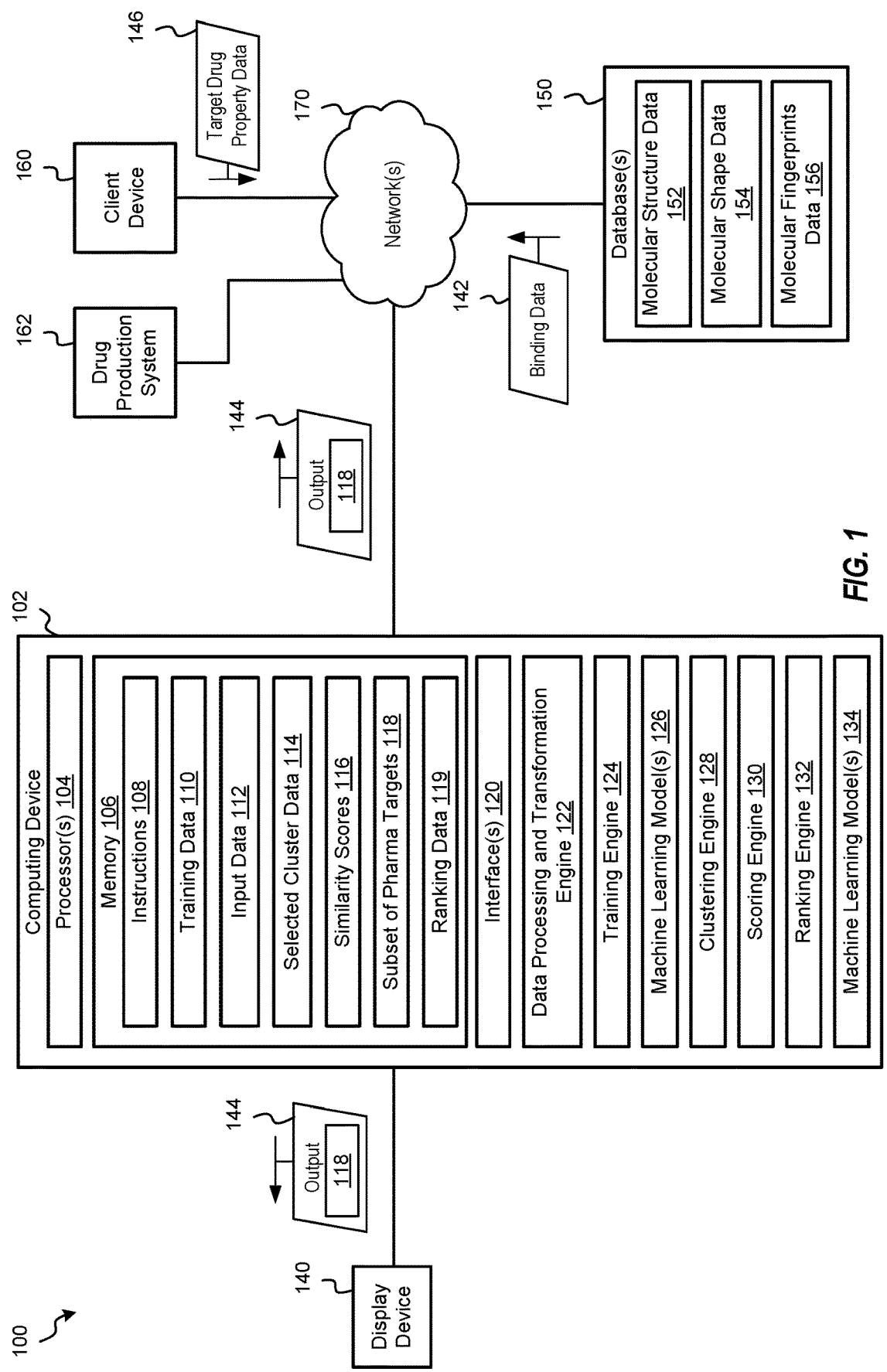
FIG. 1 is a block diagram of an example of a system for pharmaceutical molecule screening using machine learning according to one or more aspects.

It should be understood that the drawings are not necessarily to scale and that the disclosed aspects are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular aspects illustrated herein.

DETAILED DESCRIPTION

Aspects of the present disclosure provide systems, methods, and computer-readable storage media for automated screening of candidate pharmaceutical molecules or compounds using machine learning for use in pharmaceutical products such as drugs, medicine, remedies, cosmetics, and the like. The techniques described herein support automatic determination of uses (e.g., particular disease states or conditions for which the candidate pharmaceutical molecules or compounds may provide a therapeutic effect) for newly identified pharmaceutical molecules, and new uses for existing pharmaceutical molecules (e.g., previously-identified pharmaceutical molecules), using artificial intelligence and machine learning techniques. As used in the present disclosure, new or newly-identified molecules encompass molecules that may have not previously been identified, tested, and/or studied for a given pharmaceutical application (e.g., identification of new molecules for existing or new uses, disease states, or conditions and/or identification of existing molecules for new uses, disease states, or conditions). The artificial intelligence and machine learning techniques described herein may be trained using a variety of binding data associated with known pharmaceutical targets (e.g., drug targets), such as data that indicates indicate chemical properties of multiple different pharmaceutical targets, for example physiochemical structures of the pharmaceutical targets, molecular shapes of the pharmaceutical targets, molecular fingerprints of the pharmaceutical targets, and the like. The pharmaceutical targets may include proteins (e.g., protein receptors, enzymes, ion channels, etc.), nucleic acids, and the like. The binding data used for training may be obtained from a variety of sources, such as publicly available binding information databases such as the BindingDB database or the DrugBank database, the Zinc database ("Zinc15" or "Zinc12"), the SIDER database ("SIDER Side Effects Resource"), third-party databases (e.g., drug vendor or manufacturer databases, university databases, government agency databases, and the like), proprietary databases, or a combination thereof. Natural language processing may be performed on text data or particularly-formatted data, such as simplified molecular-input line-entry system (SMILES)-formatted data, to generate training data for training machine learning model(s) to assign pharmaceutical targets and candidate pharmaceutical molecules to various clusters based on chemical properties. Such clustering may reduce the search space for identifying pharmaceutical targets that will (or are likely to) bind to the candidate pharmaceutical molecules, thereby improving efficiency and reducing resource usage and costs associated with the screening process. Using artificial intelligence and machine learning that are trained based on binding data associated with large quantities of pharmaceutical targets may result in identification of pharmaceutical uses for candidate pharmaceutical molecules or compounds that would not be identified by a human (e.g., a chemist or biochemist) using existing screening processes. To illustrate, because the artificial intelligence and machine learning are able to determine underlying similarities between a wider variety of pharmaceutical targets and candidate molecules, many of which may not be apparent to a human, the systems and methods described herein may enable identification of previously unknown uses for existing pharmaceutical molecules and/or uses for newly-identified and unstudied pharmaceutical molecules. Additionally, automated identification of the pharmaceutical uses may be faster than identification performed by other systems that require substantial user interaction and decision making. By providing improved insight into pharmaceutical uses of new and existing pharmaceutical molecules in a shorter period of time, the systems and methods described herein may substantially reduce the costs and shorten the development cycle associated with discovering and launching new drugs (e.g., pharmaceuticals) or identifying new uses for existing drugs. Although described in the context of pharmaceutical products (e.g., drugs), the techniques of the present disclosure may be applied to identify uses for other types of products, such as health products and supplements, personal hygiene products, cosmetic products, biotech products, chemical products, and the like.

Referring to FIG. 1, an example of a system for pharmaceutical molecule screening using machine learning according to one or more aspects is shown as a system 100. The system 100 may be configured to train machine learning model(s) to screen "new" candidate pharmaceutical molecules or compounds (e.g., previously-unidentified molecules or compounds for use in drugs or other pharmaceutical products) and previously-identified candidate pharmaceutical molecules (e.g., known or existing pharmaceutical molecules) against multiple pharmaceutical targets to identify pharmaceutical uses for the candidate pharmaceutical molecules. To illustrate, if a candidate pharmaceutical molecule is sufficiently similar, based on chemical properties, to a particular pharmaceutical target, the candidate pharmaceutical molecule may be identified as a treatment for a disease state or condition corresponding to the pharmaceutical target. In some implementations, the system 100 may use the trained machine learning model(s) to cluster pharmaceutical targets and candidate pharmaceutical molecules based on chemical properties to reduce the amount of pharmaceutical targets to screen or otherwise score during a process performed to identify pharmaceutical uses for new and existing pharmaceutical molecules. In some implementations, the system 100 may rank a subset of pharmaceutical targets that are selected for a candidate pharmaceutical molecule or compound, such as using conjoint analysis, optionally with additional machine learning model(s) Additionally or alternatively, the trained machine learning model(s) may be provided to other devices, such as client device(s), for use in screening candidate pharmaceutical molecules. As shown in FIG. 1, the system 100 includes a computing device 102, a display device 140, one or more databases 150, a client device 160, a drug production system 162, and one or more networks 170. In some implementations, one or more of the display device 140, the client device 160, or the drug production system 162 may be optional, or the system 100 may include additional components, such as a user device, as a non-limiting example.

The computing device 102 (e.g., a pharmaceutical molecule screening device or a drug discovery device) may include or correspond to a desktop computing device, a laptop computing device, a personal computing device, a tablet computing device, a mobile device (e.g., a smart phone, a tablet, a personal digital assistant (PDA), a wearable device, and the like), a server, a virtual reality (VR) device, an augmented reality (AR) device, an extended reality (XR) device, a vehicle (or a component thereof), an entertainment system, other computing devices, or a combination thereof, as non-limiting examples. The computing device 102 includes one or more processors 104, a memory 106, one or more communication interfaces 120, a data processing and transformation engine 122 a training engine 124, one or more machine learning (ML) models 126, a clustering engine 128, a scoring engine 130, a ranking engine 132, and one or more ML models 134. In some other implementations, one or more of the components 122-134 may be optional, one or more additional components may be included in the computing device 102, or both. It is noted that functionalities described with reference to the computing device 102 are provided for purposes of illustration, rather than by way of limitation and that the exemplary functionalities described herein may be provided via other types of computing resource deployments. For example, in some implementations, computing resources and functionality described in connection with the computing device 102 may be provided in a distributed system using multiple servers or other computing devices, or in a cloud-based system using computing resources and functionality provided by a cloud-based environment that is accessible over a network, such as the one of the one or more networks 170. To illustrate, one or more operations described herein with reference to the computing device 102 may be performed by one or more servers or a cloud-based system that communicates with one or more client or user devices.

The one or more processors 104 may include one or more microcontrollers, application specific integrated circuits (ASICs), field programmable gate arrays (FPGAs), central processing units (CPUs) having one or more processing cores, or other circuitry and logic configured to facilitate the operations of the computing device 102 in accordance with aspects of the present disclosure. The memory 106 may include random access memory (RAM) devices, read only memory (ROM) devices, erasable programmable ROM (EPROM), electrically erasable programmable ROM (EEPROM), one or more hard disk drives (HDDs), one or more solid state drives (SSDs), flash memory devices, network accessible storage (NAS) devices, or other memory devices configured to store data in a persistent or non-persistent state. Software configured to facilitate operations and functionality of the computing device 102 may be stored in the memory 106 as instructions 108 that, when executed by the one or more processors 104, cause the one or more processors 104 to perform the operations described herein with respect to the computing device 102, as described in more detail below. Additionally, the memory 106 may be configured to store data and information, such as training data 110, input data 112, selected cluster data 114, similarity scores 116, a subset of pharmaceutical targets 118, and ranking data 119. Exemplary aspects of the training data 110, the input data 112, the selected cluster data 114, the similarity scores 116, the subset of pharmaceutical targets 118, and the ranking data 119 are described in more detail below.

The one or more communication interfaces 120 may be configured to communicatively couple the computing device 102 to the one or more networks 170 via wired or wireless communication links established according to one or more communication protocols or standards (e.g., an Ethernet protocol, a transmission control protocol/internet protocol (TCP/IP), an Institute of Electrical and Electronics Engineers (IEEE) 802.11 protocol, an IEEE 802.16 protocol, a 3rd Generation (3G) communication standard, a 4th Generation (4G)/long term evolution (LTE) communication standard, a 5th Generation (5G) communication standard, and the like). In some implementations, the computing device 102 includes one or more input/output (I/O) devices that include one or more display devices, a keyboard, a stylus, one or more touchscreens, a mouse, a trackpad, a microphone, a camera, one or more speakers, haptic feedback devices, or other types of devices that enable a user to receive information from or provide information to the computing device 102. In some implementations, the computing device 102 is coupled to the display device 140, such as a monitor, a display (e.g., a liquid crystal display (LCD) or the like), a touch screen, a projector, a virtual reality (VR) display, an augmented reality (AR) display, an extended reality (XR) display, or the like. Although shown as external to the computing device 102 in FIG. 1, in some other implementations, the display device 140 is included in or integrated in the computing device 102.

The data processing and transformation engine 122 may be configured to obtain binding data 142 from the databases 150 and to process, filter, or otherwise transform the binding data 142 for use by other components of the computing device 102. For example, the binding data 142 may indicate chemical properties of pharmaceutical targets, such as proteins and/or nucleic acids, and the data processing and transformation engine 122 may process and otherwise convert the binding data 142 (or a portion thereof) to a common format that may be used for analysis and training data generation. To illustrate, the data processing and transformation engine 122 may be configured to perform one or more pre-processing operations, one or more formatting operations, one or more conversion operations, one or more filtering operations, or a combination thereof, on the binding data 142 to convert the binding data 142 to a target format, to reduce a size or complexity of the binding data 142, to eliminate particular values that do not provide sufficient information, to add in missing values, or a combination thereof.

The training engine 124 may be configured to generate the training data 110 based on the processed binding data 142. For example, the training engine 124 may extract a particular set of features from the binding data 142 and group the extracted features, such as in one or more vectors, to generate the training data 110. In some implementations, the particular set of features are determined based on feature analysis of the binding data 142 and are predetermined for all types of molecule screening, or the particular set of features may be based on a type of molecule to be screened, a particular pharmaceutical use (e.g., a particular disease or condition) for which pharmaceutical molecules are to be identified, user input, other information, or a combination thereof. To extract the features, the training engine 124 may be configured to extract numerical features from numerical data, to extract categorical features from text or numerical data and convert the categorical features to numerical features, to perform natural language processing (NLP) on text data to convert text features into numerical features, or a combination thereof. In some implementations, the training engine 124 may be configured to scale or otherwise transform extracted features to a format that is useable to train ML models. After extracting the features, the training engine 124 may group or otherwise format the extracted features, such as performing vectorization on the extracted features, to generate the training data 110.

After generating the training data 110, the training engine 124 may be configured to train the one or more ML models 126 that are accessible to the training engine 124 (e.g., via storage at the memory 106 or other storage devices) based on the training data 110. The one or more ML models 126 may be trained to perform clustering to group input molecules into one of multiple different clusters based on chemical properties of the molecules. Members of the same cluster (e.g., molecules assigned to the same cluster) may have underlying chemical property similarities to the other members of the same cluster, and may have dissimilar chemical properties to members of other clusters. To illustrate, the one or more ML models 126 may be trained to assign the pharmaceutical targets indicated by the training data 110 different clusters based on their chemical properties, such as molecular structures, molecular shapes, molecular weights, molecular fingerprints, and the like. After establishing the initial clusters, the one or more ML models 126 may assign additional input molecules, such as candidate pharmaceutical molecules, to one of the clusters based on chemical properties of the additional input molecules. In some implementations, the initially established clusters after training may be fixed. In some other implementations, the initially established clusters may be modified based on additional input data, such as by dividing one or more clusters into multiple clusters, combining one or more clusters into a single cluster, establishing one or more new clusters, etc.

In some implementations, the one or more ML models 126 (referred to herein as the ML models 126) may include a single ML model or multiple ML models configured to cluster molecules based on chemical properties. In some implementations, the ML models 126 may be implemented as neural networks. In other implementations, the ML models 126 may be implemented as other types of ML models or constructs, such as support vector machines (SVMs), decision trees, random forests, regression models, Bayesian networks (BNs), dynamic Bayesian networks (DBNs), naive Bayes (NB) models, Gaussian processes, hidden Markov models (HMMs), regression models, and the like. The ML models 126 may be trained to perform the clustering using unsupervised learning techniques, semi-supervised learning techniques, supervised learning techniques, or a combination thereof. In some implementations, the ML models 126 may be configured to perform sparse subspace clustering (SSC) to assign molecules to one of the multiple clusters based on the chemical properties of the molecules and the chemical properties of the members of the clusters.

The clustering engine 128 may be configured to assign an input molecule, such as a candidate pharmaceutical molecule, to one of the multiple clusters based on the chemical properties of the input molecule and the members of the multiple clusters. For example, the clustering engine 128 may provide input data to the ML models 126 to cause the ML models 126 to assign the pharmaceutical molecules indicated by the input data to respective ones of the multiple clusters (e.g., the clusters initially established during training of the ML models 126). To generate the input data, the clustering engine 128 may generate a feature vector or other input that corresponds to one or more candidate pharmaceutical molecules indicated by user input, one or more newly-identified candidate pharmaceutical molecules identified by other ML models trained to identify new pharmaceutical molecules, one or more existing pharmaceutical molecules corresponding to drugs manufactured or sold by a client, one or more new or existing pharmaceutical molecules identified based on other criteria, or a combination thereof.

The scoring engine 130 may be configured to generate scores associated with one of more pharmaceutical targets that are members of a cluster to which an input molecule, such as a candidate pharmaceutical molecule, is assigned. In some implementations, the scoring engine 130 may be configured to generate a composite score for each of the pharmaceutical targets that are members of the cluster to which the candidate pharmaceutical molecule is assigned. Each composite score may be based on one or more comparisons between the candidate pharmaceutical molecule and the respective pharmaceutical target. For example, the scoring engine 130 may be configured to perform similarity measurements between one or more molecular fingerprints associated with the candidate pharmaceutical molecule and one or more molecular fingerprints associated with the respective pharmaceutical target. The similarity measurements may include a Tanimoto coefficient, a cosine similarity, a largest common string (LCS) similarity, a Library for the Enumeration of Modular Natural Structures (LEMONS)-based similarity, a retrobiosynthesis and alignment (GRAPE) similarity, an intrinsic solubility (log S) similarity, a Delaney dataset similarity, a half maximal inhibitory concentration (IC50) similarity, a half maximal effective concentration (EC50) similarity, a partition between lipid and aqueous phases (log D) similarity, a hydrogen bond (H-bond) similarity, an aromaticity similarity, a simplified molecular-input line-entry system (SMILES)-based similarity, other similarity measurements, or combination thereof. The composite score may be an average score, or other aggregate score, based on the similarity measurements. In some implementations, the scoring engine 130 may be configured to identify one or more of the pharmaceutical targets that are members of the cluster based on the composite scores. For example, the scoring engine 130 may be configured to compare the composite scores to one or more thresholds to identify a subset of the pharmaceutical targets that are associated with composite scores that satisfy the one or more thresholds.

The ranking engine 132 may be configured to rank the pharmaceutical targets identified by the scoring engine 130 (e.g., the subset of pharmaceutical targets). In some implementations, the ranking engine 132 may be configured to perform conjoint analysis on the subset of pharmaceutical targets and the candidate pharmaceutical molecule. To illustrate, the ranking engine 132 may be configured to obtain target drug property data 146, such as from the client device 160 and/or other sources, that indicates information associated with target or desired drugs for a client. As a non-limiting example, the ranking engine 132 may be configured to generate and provide survey documents to the client device 160 and to receive response data (e.g., the target drug property data 146, or a portion thereof) from the client device 160. To illustrate, the survey documents may include questions that ask the client to select a preferred drug (or drug property) from amongst two or more drugs (or drug properties), and the target drug property data 146 may indicate the preferred drugs (or drug properties). As other examples, the ranking engine 132 may be configured to extract the target drug property data from pharmaceutical news data, market research, pharmaceutical press releases, or the like, that indicates preferred drugs or properties by the client, by the market, etc., or by receiving user input data from the client device 160 that indicates the target drug property data 146. The ranking engine 132 may be configured to analyze the target drug property data 146 to identify the preferred drug properties and to rank the subset of pharmaceutical targets (e.g., drugs formed by combining the candidate pharmaceutical molecule with the subset of pharmaceutical targets) based on the preferred drug properties.

In some implementations, the ranking engine 132 may be configured to perform the ranking using the one or more ML models 134 that are accessible to the ranking engine 132 (e.g., via storage at the memory 106 or other storage devices). To illustrate, the ranking engine 132, the training engine 124, or both may be configured to generate training data (referred to herein as "second training data") based on the target drug property data 146, such as by extracting features from the target drug property data 146, combining the extracted vectors into one or more feature vectors (or other formats), labelling the feature vectors based on overall scores associated with information indicated by the extracted features, and using the labelled feature vectors as the second training data (e.g., labelled training data). After generating the second training data, the training engine 124, the ranking engine 132, or both, may be configured to train the one or more ML models 134 based on the second training data. The one or more ML models 134 may be trained to predict a score associated with an input (e.g., a drug formed by combining a pharmaceutical target and a candidate pharmaceutical molecule), such as by performing regression or classification, as non-limiting examples.

In some implementations, the one or more ML models 134 (referred to herein as the ML models 134) may include a single ML model or multiple ML models configured to predict scores associated with combinations of candidate pharmaceutical molecules and pharmaceutical targets based on scores of drugs indicated by the target drug property data 146 and similarity between the pharmaceutical targets and the drugs. In some implementations, the ML models 134 may be implemented as neural networks. In other implementations, the ML models 134 may be implemented as other types of ML models or constructs, such as SVMs, decision trees, random forests, regression models, BNs, DBNs, NB models, Gaussian processes, HMMs, regression models, and the like. The ML models 134 may be trained to predict the scores using supervised learning techniques, semi-supervised learning techniques, unsupervised learning techniques, or a combination thereof.

The databases 150 may include one or more databases, or other storage devices, configured to maintain and provide access to stored binding data. The databases 150 may include publically available binding information databases (e.g., databases maintained by information or standards organizations or government agencies such as the Food and Drug Administration (FDA), the Center for Disease Control (CDC), and the like), third-party binding information databases (e.g., databases maintained by pharmaceutical vendors or researchers, universities, and the like), proprietary databases (e.g., databases maintained by an entity that operates the computing device 102), other databases, or a combination thereof. Particular, non-limiting examples of publically available or accessible databases include the BindingDB database, the DrugBank database, the Therapeutic Targets Database, the ZINC database, the chEMBL database, the PubChem database, the Zinc database ("Zinc15" or "Zinc12"), the SIDER database ("SIDER Side Effects Resource"), and the like.

The databases 150 are configured to store the binding data 142 that indicates chemical properties, such as physiochemical structures, molecular shapes, molecular fingerprints, and the like, associated with multiple pharmaceutical targets (e.g., proteins, nucleic acids, etc.). In some implementations, the databases 150 are configured to store (e.g., the binding data 142 includes) molecular structure data 152, molecular shape data 154, molecular fingerprints data 156, other binding data, or a combination thereof. The molecular structure data 152 may indicate physiochemical structures of the pharmaceutical targets, such as the elements and connections of the elements (or compounds), that form the pharmaceutical targets. In some implementations, at least a portion of the molecular structure data 152 may be formatted in accordance with the simplified molecular-input line-entry system (SMILES). SMILES is a line notation for describing the structure of chemical species using short ASCII strings that include letters and numbers indicating elements (and their respective quantity) and other symbols (e.g., . - =# $ : / \) that represent different types of bonds between the elements. As an example, a molecule of carbon dioxide may be represented as O=C=O in the SMILES notation. The SMILES notation is designed such that a molecule represented by a SMILES notation can be easily converted to a two-dimensional or three-dimensional model of the respective molecule. The molecular shape data 154 may indicate the molecular shape of the pharmaceutical targets, such as the three-dimensional geometric shape of the molecules, bond lengths, bond angles, torsional angles, and the like. The molecular fingerprints data 156 may indicate fingerprints representing the pharmaceutical targets, such as substructure fingerprints, atom-pair fingerprints, and the like. The above-described types of binding data are not intended to be limiting, and in other implementations, other types of binding data may be stored by the databases 150.

The client device 160 may include or correspond to a computer device used by a client of the entity that operates the computing device 102 to perform molecule screening (e.g., drug screening/searching). For example, the client device 160 may be operated by a pharmaceutical company, a university, a research institution, or the like, that is engaged in drug screening. The client device 160 may include or correspond to a computing device, such as a desktop computer or a laptop computer, a server, a mobile device (e.g., a smart phone, a tablet computer, a wearable device, a personal digital assistant (PDA), or the like), an audio/visual device, an entertainment device, a control device, a vehicle (or a component thereof), a VR device, an AR device, an XR device, or the like. The client device 160 may be configured to receive the trained ML models 126 (or configuration data associated with the trained ML models 126), the trained ML models 134 (or configuration data associated with the trained ML models 134), or both, for use in the drug screening and ranking process.

The drug production system 162 may include one or more automated or semi-automated equipment or devices configured to perform operations of drug formulation. For example, the drug production system 162 may include or correspond to agitators, blowers, boilers, centrifuges, chillers, cooling towers, dryers, homogenizers, mixers, ovens, and the like. Components of the drug production system 162 may include processors, memories, interfaces, motors, sensors, and the like that are configured to enable fully or semi-automated performance of one or more operations, in addition to communication with other components of the drug production system 162 or other devices. In some implementations, the drug production system 162 may be configured to receive instructions from the computing device 102 for initiating one or more operations.

During operation of the system 100, the computing device 102 may obtain the binding data 142 from the databases 150. For example, the computing device 102 may query the databases 150 and receive the binding data 142 (or a portion thereof). As another example, the computing device 102 may manually pull the binding data 142 (or a portion thereof) from the databases 150 using one or more pull commands. As another example, the computing device 102 may extract the binding data 142 (or a portion thereof) from websites or other publically accessible information displays that are supported by the databases 150, such as using a crawler or other data mining techniques. As described above, the binding data 142 may indicate properties of multiple pharmaceutical targets, such as proteins and nucleic acids, as non-limiting examples. In some implementations, the binding data 142 may include the molecular structure data 152, the molecular shape data 154, the molecular fingerprints data 156, other types of binding data, or a combination thereof.

The data processing and transformation engine 122 may process and transform the binding data 142, such as transforming different types of data included in the binding data 142 to a common format or type. In some implementations, the data processing and transformation engine 122 may perform pre-processing on the binding data 142. Performing the pre-processing may reduce complexity of feature extraction to be performed on the binding data 142, reduce the memory footprint associated with the binding data 142, clean up the binding data 142, format the binding data 142, or a combination thereof. For example, the pre-processing may include performing statistical analysis on the binding data 142 to remove or modify an outlier from the binding data 142, removing an entry from the binding data 142 that is associated with a variance that fails to satisfy a variance threshold, formatting the binding data 142, approximating a missing entry of the binding data 142 (e.g., using interpolation or other statistical modeling techniques), other pre-processing operations, or a combination thereof. Additionally or alternatively, the data processing and transformation engine 122 may perform dimensionality reduction on the binding data 142 (or extracted features) to reduce a memory footprint associated with the binding data 142 and to reduce processing complexity of the feature extraction performed by the training engine 124. The dimensionality reduction may project the binding data 142 onto a lower-dimension feature space, such as by primary component analysis, singular value decomposition, or the like.

The training engine 124 may generate the training data 110 based on the processed binding data 142 from the data processing and transformation engine 122. Generating the training data 110 may include extracting a predetermined set of features from the binding data 142, which may include performing one or more operations to convert the binding data 142 to a different type of data from which features that are acceptable to the ML models 126 may be extracted. In some implementations, the training engine 124 may extract numerical features from the binding data 142. For example, the numerical features may include atomic weights, molecular weights, numbers of links, or the like. The training engine 124 may scale or otherwise transform the extracted numerical features, such as performing a normalization transformation, a standardization transformation, a power transformation, a quantile transformation, or a combination thereof, on the extracted numerical features. Additionally or alternatively, the training engine 124 may extract numerical features from non-numerical features in the binding data 142. As an example, the training engine 124 may convert categorical features or binary features to integer values, such as '1' or '0' for 'yes' and 'no,' respectively, or create integer values from multiple different categories, such as using a one-hot encoding. As another example, the training engine 124 may perform NLP on text data of the binding data 142 to convert the text data into numerical features. The NLP may include tokenization, removing stop words, stemming, lemmatization, bag of words processing, other NLP, or a combination thereof. In some implementations, at least a portion of the binding data 142, such as the molecular structure data 152, may be SMILES-formatted text data. For example, physiochemical structures of the previously-identified molecules may be represented by strings of characters according to the SMILES notation, such as O=C=O for carbon dioxide. In such implementations, the training engine 124 may perform NLP on the SMILES-formatted strings to convert the SMILES-formatted strings to numerical features, such as numbers of various elements, numbers of various types of bonds, correspondence between the bonds and the elements, etc. As other example, the training engine 124 may perform NLP on text data included in the binding data 142 to extract numerical features corresponding to other textual information, such as receptor information, molecular shapes, and the like. After extracting the features, the training engine 124 may vectorize or otherwise group the extracted features to a format that may be processed by the ML models 126 to generate the training data 110.

After generating the training data 110, the training engine 124 may train the ML models 126 to cluster molecules into chemical property-related clusters based on the training data 110. In some implementations, training the ML models 126 may include segmenting the training data 110 into a training set and a test set. The training engine 124 may provide the training set to the ML models 126 to train the ML models 126 to cluster molecules (e.g., the pharmaceutical targets indicated by the binding data 142) based on underlying similarities between molecules. In addition to, or as part of the training, the training engine 124 may adjust one or more parameters or hyper-parameters associated with the ML models 126. In some implementations, the training engine 124 may train the ML models 126 to perform sparse subspace clustering (SSC) to cluster the molecules based on chemical properties The clustering may group the pharmaceutical targets into multiple different clusters that have similar chemical properties, such as molecular structures or shapes, or the like. In some implementations, the clustering may include density-based spatial clustering of applications with noise (DBSCAN), K-means clustering, K-means for large-scale clustering (LSC-K), longest common subsequence (LCS) clustering, longest common cyclic subsequence (LCCS) clustering, or the like, in order to cluster large volumes of high dimensional data.

In some implementations, after the training engine 124 trains the ML models 126, the clustering engine 128 may access the ML models 126 to assign one or more candidate pharmaceutical molecules to the established clusters based on chemical properties of the candidate molecules. For example, the clustering engine 128 may provide the input data 112 that indicates a candidate pharmaceutical molecule (or multiple candidate pharmaceutical molecules) to the ML models 126 to assign the candidate pharmaceutical molecule to a cluster which includes members (e.g., pharmaceutical targets) that have the most similar chemical properties to the candidate pharmaceutical molecule. In some implementations, the candidate pharmaceutical molecule may be a newly identified molecule, such as by one or more generative ML models, as further described herein with reference to FIG. 3. Additionally or alternatively, the candidate pharmaceutical molecule may be a previously-identified molecule for which a new pharmaceutical use is desired to be tested. Such previously-unidentified new uses may include molecules that are known for being useful for one disease state or condition (e.g., cancer) to a discovered new disease state or condition (e.g., diabetes).

In some implementations, the input data 112 may indicate chemical or physical (e.g., physiochemical) properties of the candidate pharmaceutical molecule, such as by including features that indicate the molecular structure, the molecular shape, molecular fingerprints, other properties, and the like, associated with the candidate pharmaceutical molecule. The clustering engine 128 may generate the selected cluster data 114 that indicates the members (e.g., the pharmaceutical targets) of the cluster to which the candidate pharmaceutical molecule is assigned. For example, the selected cluster data 114 may indicate the names of the pharmaceutical targets, as well as other information associated with the pharmaceutical targets, such as molecular structures, molecular shapes, molecular fingerprints, and the like. Additionally or alternatively, the selected cluster data 114 may indicate the pharmaceutical targets that are associated with each of the established clusters (e.g., the selected cluster data 114 may instead include data for all the established clusters).

After assigning the candidate pharmaceutical molecule indicated by the input data 112 to a cluster associated with the selected cluster data 114, the scoring engine 130 may determine the similarity scores 116 by comparing the candidate pharmaceutical molecule to the pharmaceutical targets that are members of the cluster. To illustrate, the similarity scores 116 may include, for each pharmaceutical target indicated by the selected cluster data 114, a respective composite score. The composite scores may be determined based on one or more comparisons between the candidate pharmaceutical molecule and each of the pharmaceutical targets. To illustrate, the scoring engine 130 may generate similarity measurements based on comparisons of molecular fingerprints associated with the candidate pharmaceutical molecule and molecular fingerprints of a first pharmaceutical target indicated by the selected cluster data 114, and the scoring engine 130 may generate the composite score as an average of the similarity measurements. For example, the scoring engine 130 may compare molecular fingerprints associated with the candidate pharmaceutical molecule and the first pharmaceutical target to generate a Tanimoto coefficient and a cosine similarity value, and the scoring engine 130 may generate a first composite score associated with the first pharmaceutical target based on an average of the Tanimoto coefficient and the cosine similarity value (optionally processed to a common format or weighted based on importance of particular similarity measurements). As other non-limiting examples, the similarity measurements may include LCS similarities, LEMONS-based similarities, GRAPE similarities, log S similarities, Delaney dataset similarities, IC50 similarities, EC50 similarities, log D similarities, H-bond similarities, aromaticity similarities, SMILES-based similarities, or combination thereof. In some other implementations, the composite score (e.g., the similarity scores 116) may include a different aggregate score, such as a sum, a maximum value, a median value, a mode, a weighted average, or the like.

After generating the similarity scores 116 (e.g., the composite scores), the scoring engine 130 may identify a subset of pharmaceutical targets 118 associated with the cluster based on the similarity scores 116. To illustrate, the scoring engine 130 may compare the similarity scores 116 to one or more thresholds to identify the subset of pharmaceutical targets 118 that are associated with similarity scores that satisfy the one or more thresholds. As used herein, satisfying a threshold refers to a value that is greater than or equal to a threshold value. In other implementations, satisfying a threshold may occur if a value is greater than a threshold value, if the value is less than the threshold value, or if the value is less than or equal to the threshold value, depending on the context. The subset of pharmaceutical targets 118 may be referred to as the screened or searched pharmaceutical targets that are most likely to bind with the candidate pharmaceutical molecule and form a useful drug or other pharmaceutical product.

The ranking engine 132 may rank the subset of pharmaceutical targets 118 (e.g., order a list of the subset of pharmaceutical targets 118 by determined rankings) based on the target drug property data 146. In some implementations, ranking the subset of pharmaceutical targets 118 may include performing conjoint analysis on the subset of pharmaceutical targets 118, the candidate pharmaceutical molecule, and the target drug property data 146. The conjoint analysis may be performed by segregating properties of drugs that may be formed by combining the candidate pharmaceutical molecule with the subset of pharmaceutical targets 118 into different combinations of properties, such as primary effects, side effects, toxicity, price, and the like, and determining the preferences for the properties by the client (and/or consumers, the marketplace, other drug manufacturers, etc.). As a non-limiting example, the ranking engine 132 may generate survey or questionnaire documents that ask a client (or others) to indicate preferences for various combinations of properties, and the target drug property data 164 may indicate the preferences. In such an example, the ranking engine 132 may analyze the preferences indicated by the target drug property data 164 to determine which properties, or combinations of properties, are more preferable, and to rank pharmaceutical targets having the more preferable properties higher than others of the subset of pharmaceutical targets 118. As another example, the ranking engine 132 may obtain the target drug property data 164 by crawling (or using other data mining techniques) to extract the information from pharmaceutical news data, market research, pharmaceutical press releases, other publically-available or proprietary pharmaceutical information sources, or a combination thereof. To illustrate, the ranking engine 132 may extract target drug properties associated with drugs described as in-demand or high selling in financial publications, newly released drugs described in newspapers, message boards, online articles, press releases, and the like, currently researched drugs described in medical journals, research publications, and the like, or a combination thereof.

The ranking engine 132 may rank the subset of pharmaceutical targets 118 based on the target drug property data 164 to generate the ranking data 119. To illustrate, the ranking engine 132 may generate the ranking data 119 that indicates an ordered ranking of the subset of pharmaceutical targets 118 based on the preference of the client (or others) for properties associated with a respective pharmaceutical target (or an expected combination of the candidate pharmaceutical molecule and the respective pharmaceutical target). For example, the ranking data 119 may indicate the order of pharmaceutical targets of the subset of pharmaceutical targets 118 based on the client preferences, or the ranking engine 132 may re-order the subset of pharmaceutical targets 118 based on the rankings indicated by the ranking data 119. Additionally or alternatively, the ranking data 119 may indicate estimate ranks (e.g., scores) associated with one or more of the subset of pharmaceutical targets 118. In some implementations, the ranking engine 132 may provide input data indicating the subset of pharmaceutical targets 118 and the candidate pharmaceutical molecule to the ML models 134 to generate the ranking data 119. To illustrate, the ranking engine 132 (and/or the training engine 124) may train the ML models 134 to rank pharmaceutical targets based on preferences indicated by the target drug property data 146. For example, the target drug property data 146 may include drug property preferences and historical rankings of previously-manufactured drugs, and such data may be used as training data to train the ML models 134 to rank pharmaceutical targets (or combinations of the candidate pharmaceutical molecule and pharmaceutical targets) based on similarities of the pharmaceutical targets (or combinations) to one or more highly-ranked drugs, highly-ranked drug properties, etc.

After identifying the subset of pharmaceutical targets 118, and optionally ranking the subset of pharmaceutical targets 118, the computing device 102 may generate an output 144 that indicates the subset of pharmaceutical targets 118 and the candidate pharmaceutical molecule indicated by the input data 112. The output 144 may be displayed to a user, provided to another device, or used to initiate performance of one or more operations. As an example, the computing device 102 may provide the output 144 to the display device 140 to cause the display device 140 to display a graphical user interface (GUI). The GUI may include text indicating the subset of pharmaceutical targets 118 (e.g., names of the subset of pharmaceutical targets 118, SMILES strings indicating the physiochemical structure of the subset of pharmaceutical targets 118, disease conditions known to be treated by the subset of pharmaceutical targets 118, and the like), visual representations of the subset of pharmaceutical targets 118 (e.g., 2D or 3D representations of the respective molecular structures), other text or multimedia content representing the subset of pharmaceutical targets 118, or a combination thereof, in addition to, or in the alternative to, similar information associated with the candidate pharmaceutical molecule. Additionally or alternatively, the GUI may include text, graphical, or multimedia content that indicates properties of the subset of pharmaceutical targets 118 and the candidate pharmaceutical molecule (e.g., a drug formed from a combination of the candidate pharmaceutical molecule and a respective pharmaceutical target), such as a list of side effects, solubility measurements, toxicity measurements, likely impacted organs, and the like, and/or comparisons of the properties of the subset of pharmaceutical targets 118 and the candidate pharmaceutical molecule to properties of previously-manufactured drugs or other pharmaceuticals, such as graphs, charts, or the like. In some implementations, the subset of pharmaceutical targets 118 may be displayed in a ranked order and/or the ranking data 119 may also be displayed within the GUI. As another example, the computing device 102 may provide the output 144 to another device, such as the client device 160 or a user device. As another example, the computing device 102 may provide the output 144 to the drug production system 162 to initiate performance of one or more operations at the drug production system 162. To illustrate, the output 144 may include or correspond to one or more instructions that cause the drug production system 162 to perform one or more operations to facilitate formation of drugs based on combinations of the candidate pharmaceutical molecule and the subset of pharmaceutical targets 118. For example, the one or more instructions may initiate mixing of chemicals in a mixer, activating a heater or a cooler to change a state of a chemical, retrieving of one or more samples from a vault or other storage location, or the like.

Additionally or alternatively, the computing device 102 may provide the trained ML models 126 to the client device 160. For example, after training the ML models 126, the computing device 102 may generate configuration information that indicates the parameters, the hyper-parameters, and any other configuration of the trained ML models 126, and the computing device 102 may provide the configuration information to the client device 160 to enable the client device 160 to implement the trained ML models 126 at the client device 160 for screening candidate pharmaceutical molecules as part of drug discovery performed at the client device 160. In some implementations, the computing device 102 may be configured to train the ML models 126 but not to perform the screening process, instead leaving the screening process to be performed by the client device 160. In such implementations, the computing device 102 does not include the clustering engine 128. Additionally or alternatively, the computing device 102 may train the ML models 134 and provide the trained ML models 134 (or configuration information associated with the ML models 134) to the client device 160 to enable the client device 160 to implement the trained ML models 134 at the client device 160 for ranking pharmaceutical targets to be combined with candidate pharmaceutical molecules.

As described above, the system 100 supports training of the ML models 126 to automatically assign candidate pharmaceutical molecules into one of multiple clusters based on similarities between the chemical or physical properties of the candidate pharmaceutical molecule and chemical or physical properties of pharmaceutical targets that are members of the cluster. Using artificial intelligence and machine learning to assign the candidate pharmaceutical molecule to a particular cluster limits the search space for screening the candidate pharmaceutical molecule, which may increase speed and reduce resources of the remainder of the screening process (e.g., scoring the pharmaceutical targets corresponding to the cluster and identifying the subset of pharmaceutical targets 118). Such operations may enable the discovery of pharmaceutical uses for newly-identified pharmaceutical molecules, or new uses of existing pharmaceutical molecules, without requiring analysis and scoring of the approximately $10^{60}$ existing pharmaceutical targets for combing with the pharmaceutical molecules. Additionally or alternatively, using artificial intelligence and machine learning that is trained using a large amount of binding data as training data may enable learning of underlying relationships between chemical or physical properties of pharmaceutical targets that would not be apparent to human drug experts due to their limited experience and knowledge, or their focus on finding a relationship to a particular pharmaceutical target for treating a particular disease state. Generating the ranking data 119 and/or ranking the subset of pharmaceutical targets 118 may also reduce the cycle time and cost associated with selecting the most commercially successful drugs to test. Thus, the system 100 may substantially reduce the costs and shorten the development cycle associated with discovering and launching new drugs or pharmaceutical products, or with discovering new pharmaceutical uses for existing pharmaceutical molecules.

Figure 2:
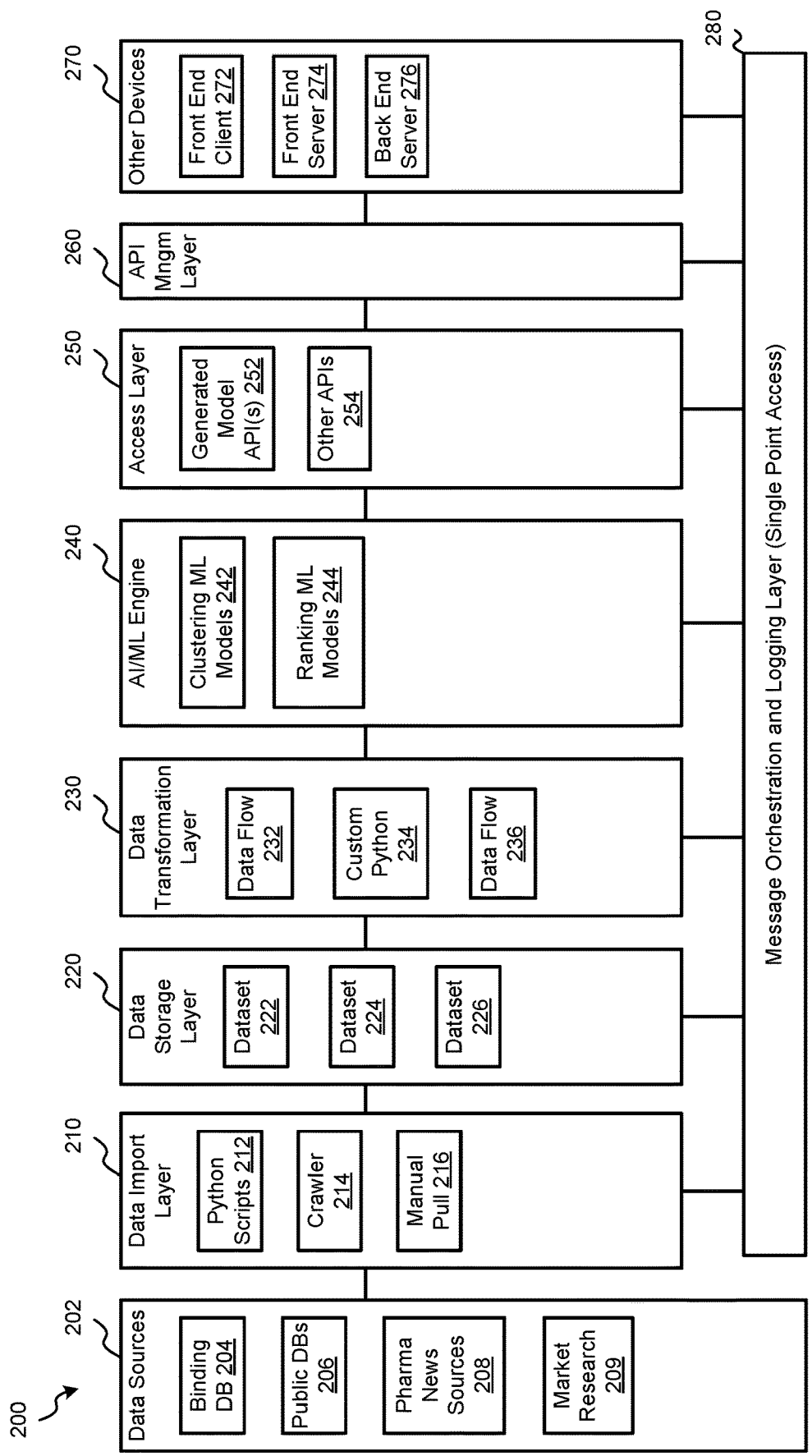
FIG. 2 is a block diagram of another example of a system for pharmaceutical molecule screening using machine learning according to one or more aspects.

Referring to FIG. 2, another example of a system for pharmaceutical molecule screening using machine learning according to one or more aspects is shown as a system 200. In some implementations, the system 200 may include or correspond to the system 100 of FIG. 1. As shown in FIG. 2, the system 200 (also referred to as a drug screening platform) includes data sources 202, a data import layer 210, a data storage layer 220, a data transformation layer 230, an artificial intelligence/machine learning (AI/ML) engine 240, an access layer 250, an application programming interface (API) management layer 260, other devices 270, and a message orchestration and logging layer 280.

The data sources 202 include multiple data sources, such as databases, for accessing binding data for use in training ML models to cluster pharmaceutical targets as part of a screening process. In the particular implementation illustrated in FIG. 2, the data sources 202 may include a BindingDB database 204, public databases 206, pharmaceutical news sources 208, and market research 209. In other implementations, the data sources 202 may include other data sources, such as other publically available databases, third party databases, proprietary databases, or a combination thereof, as further described with reference to FIG. 1. The BindingDB database 204 is a publically available database that maintains binding data of multiple pharmaceutical targets (e.g., drug targets), such as various proteins and nucleic acids, as non-limiting examples. The public databases 206 may include other publically available databases that maintain binding data for multiple pharmaceutical targets, such as the DrugBank database or the Therapeutic Targets Database, as non-limiting examples. The pharmaceutical news sources 208 may store articles, press releases, journals, whitepapers, and the like, associated with pharmaceutical companies, pharmaceutical research, drug releases, and the like. The market research 209 may store articles, stock prices, revenue information, and the like associated with pharmaceutical companies or particular pharmaceutical products.

The data import layer 210 may be configured to import (e.g., obtain) binding data from the data sources 202 for use as training data. The data import layer 210 may be configured to request and receive the binding data from the data sources 202, to extract the binding data from information supported by the data sources 202, to pull the binding data from the data sources 202, or a combination thereof. For example, the data import layer 210 may include Python scripts 212, a crawler 214, and manual pull logic 216. The Python scripts 212 may be executable scripts in Python (or another scripting language) that, when executed by the data import layer 210, cause the data import layer 210 to request and/or query the data sources 202 for various binding data. In some implementations, the Python scripts 212 may be configured to interact with one or more application programming interfaces (APIs) of the data sources 202 to receive the binding data. The crawler 214 may include or correspond to a web crawler, or other data mining application, that is configured to extract binding data from websites (or other sources) that are supported by the data sources 202. The manual pull logic 216 may be configured to perform one or more pull operations with respect to the data sources 202 to retrieve binding data.

The data storage layer 220 may be configured to store the imported (e.g., obtained) binding data from the data sources 202. For example, the data storage layer 220 may store the binding data as one or more datasets, such as a first dataset 222, a second dataset 224, and a third dataset 226, as shown in FIG. 2. In other implementations, the binding data may be stored as fewer than three datasets or more than three datasets. The datasets 222-226 may correspond to different types of data (e.g., molecular structure data, molecular shape data, molecular fingerprints data, etc.), different types of pharmaceutical targets or targeted diseases, different properties (e.g., particular molecular structures, particular molecular shapes, etc.), or may be segregated in other manners. In some implementations, the datasets 222-226 may be stored at one or more cloud storage locations for further analysis and retained in different source folders for downstream component analysis.

The data transformation layer 230 may be configured to pre-process and transform the stored binding data (e.g., the datasets 222-226) into a format that can be used as training data for ML models. The data transformation layer 230 may include a first data flow 232, custom Python scripts 234, and a second data flow 236. In other implementations, the data transformation layer 230 may include a single data flow or more than two data flows, different types of scripts for processing and transforming data, or a combination thereof. The first data flow 232 and the second data flow 236 may correspond to particular datasets, such as the first dataset 222 and the second dataset 224, respectively. The custom Python scripts 234 may be configured to perform pre-processing operations, transformation operations, feature extraction operations, training data generation operations, or a combination thereof. For example, the custom Python scripts 234 may be configured to perform statistical analysis on the binding data to remove or modify an outlier from the binding data, remove an entry from the binding data that is associated with a variance that fails to satisfy a variance threshold, format the binding data, approximate a missing entry of the binding data (e.g., using interpolation or other statistical modeling techniques), perform other pre-processing operations, or a combination thereof. Additionally or alternatively, the custom Python scripts 234 may be configured to perform dimensionality reduction on the binding data to reduce a memory footprint associated with the binding data and to reduce processing complexity of the feature extraction. The dimensionality reduction may project the binding data onto a lower-dimension feature space, such as by primary component analysis, singular value decomposition, or the like. The custom Python scripts 234 may be configured to extract numerical features from the processed binding data, or perform operations to convert text data to numerical features. For example, the custom Python scripts 234 may perform NLP on text data to convert the text data into numerical features. The NLP may include tokenization, removing stop words, stemming, lemmatization, bag of words processing, other NLP, or a combination thereof. After extracting the features, the custom Python scripts 234 may vectorize or otherwise group the extracted features to a format that may be processed by ML models to generate training data.

The AI/ML engine 240 may be configured to train and support one or more ML models to screen candidate pharmaceutical molecules against known pharmaceutical targets to identify one or more uses for the candidate pharmaceutical molecules. In some implementations, the AI/ML engine 240 may support one or more clustering ML models 242, one or more ranking ML models 244, or a combination thereof. In other implementations, the AI/ML engine 240 may support fewer ML models, more ML models, or different ML models. In some implementations, the one or more clustering ML models 242, the one or more ranking ML models 244, or a combination thereof, may be implemented using neural networks (e.g., convolutional neural networks, deep neural networks, neural networks with hidden layers, and the like). In some other implementations, the one or more clustering ML models 242, the one or more ranking ML models 244, or a combination thereof, may be implemented using other types of ML models or structures, such as SVMs, decision trees, random forests, regression models, BNs, DBNs, NB models, Gaussian processes, HMMs, and the like.

The AI/ML engine 240 may be configured to receive training data from the data transformation layer 230 and to provide the training data to the ML models 242-244 to train the ML models 242-244 to cluster candidate pharmaceutical molecules based on chemical or physical properties and to rank pharmaceutical targets, as described with reference to FIG. 1. In some implementations, training the ML models 242-244 may include keeping aside a portion of the received data as test data to test performance of the trained ML models (e.g., to identify whether additional training should be performed, or to identify which of multiple ML models performs the best). In some implementations, different ML models of the ML models 242-244 may be trained differently (e.g., using different training data) than others of the ML models 242-244. For example, the clustering ML models 242 may be trained using training data that indicates chemical or physical properties of pharmaceutical targets. As another example, the ranking ML models 244 may be trained using training data that indicates client preferences and historical rankings. In some implementations, the clustering ML models 242 and the ranking ML models 244 may be trained to perform heuristic optimization for content filtering, binary searching for ranking pharmaceutical molecules to pharmaceutical targets, and indexing using ligand and pharmaceutical target identifiers.

In some implementations, the clustering ML models 242 may be configured to screen/search candidate search molecules across existing pharmaceutical target molecules. To perform the screening/searching, the binding data may be clustered to enable subset searching for a given candidate pharmaceutical molecule and scoring of the identified pharmaceutical targets. In some implementations, the clustering ML models 242 may be configured to perform sparse subspace clustering (SSC). SSC is a version of subspace clustering, which has as an aim to find subspaces in which data samples lie by posing the clustering problem as a regression problem. SSC typically has good performance in different application areas and theoretical guarantees. SSC is based on the idea that data points that lie in a linear subspace can be linearly represented by other data points located in the same subspace. Coefficients that represent these subspaces, which may be determined using least absolute shrinkage and selection operator (LASSO) analysis, reflect the similarity between different data points and may be used to construct an affinity matrix. Spectral clustering may be applied to this affinity matrix to identify different clusters. Thus, the success of SSC may depend mainly on three properties of the data to be clustered: 1.) low affinity between subspaces; 2.) enough samples for a certain subspace; and 3.) the data not having too many outliers (e.g., data points that do not lie within any of the subspaces).

In some such implementations, SSC may be posed as an L1 minimization problem over the subspace coefficients, given by Formula 1 below, where y contains the coefficients of the subspace and S_ contains all (vectorized) USVs in its column, except for USV s, where U and V are orthogonal matrices and S is a diagonal matrix consisting of singular values.

SSC as an L1 Minimization Problem $$\min_y \|Y\|_1 \text{ s.t. } s = S * y \quad \quad \text{Formula 1}$$

An equivalent formulation using LASSO is given by Equation 2 below.

SSC using LASSO $$\min_y \frac{1}{2}\|s - s*y\|_2^2 + \lambda\|y_1\| \quad \quad \text{Formula 2}$$

Formula 2 may be rewritten, as Formula 3 below, in matrix form to include all USVs si i ∈ {1, ..., N}, where diag(Y) is a vector with the diagonal elements of Y. Each column of S contains a vocalization and each column of Y contains the coefficients for the different USVs.

SSC using LASSO in Matrix Form $$\min_y \frac{1}{2}\|S - SY\|_2^2 + \lambda\|Y_1\| \text{ s.t. diag}(Y) = 0 \quad \quad \text{Formula 3}$$

From Y, the similarity matrix A may be computed by Formula 4 below.

$$A = |Y| + |Y|^T \quad \quad \text{Formula 4—Example Similarity Matrix}$$

Outlier detection may be performed by Formula 5 below.

Example Outlier Detection $$\max_{s \neq s'} \cos(s, s') < \tau \text{ where } \cos(s, s') = \frac{s' \cdot s}{\|s\| * \|s'\|} \quad \quad \text{Formula 5}$$

After the pharmaceutical targets are clustered by the clustering ML models 242, input data indicating a candidate pharmaceutical molecule may be provided to the clustering ML models 242 to assign the candidate pharmaceutical molecule to one of the existing clusters, as described above with reference to FIG. 1. After assigning the candidate pharmaceutical molecule to a cluster, the pharmaceutical targets that are members of the cluster (e.g., the identified cluster) may be scored by comparing one or more molecular fingerprints of the candidate pharmaceutical molecule to corresponding molecular fingerprints of respective pharmaceutical target to generate one or more similarity scores associated with the respective pharmaceutical target, and the similarity scores may be combined, such as by averaging or another composite operation, to generate a composite score associated with the respective pharmaceutical target. The similarity scores may be based on a variety of different comparisons. As a particular example, the candidate pharmaceutical molecule and a pharmaceutical target may be compared based on a Tanimoto coefficient (e.g., Tanimoto score) given by Equation 1 below.

Tanimoto coeffiecient $$J'_\omega(x, y) = \frac{\sum_i \min(x_i, y_i)}{\sum_i \max(x_i, y_i)} \quad \quad \text{Equation 1}$$

As another particular example, the candidate pharmaceutical molecule and a pharmaceutical target may be compared based on a cosine similarity given by Equation 2 below.

Cosine Similarity $$\text{similarity} = \cos(\theta)\frac{A \cdot B}{\|A\|\|B\|} = \frac{\sum_{i=1}^{n} A_i B_i}{\sqrt{\sum_{i=1}^{n} A_i^2} \sqrt{\sum_{i=1}^{n} B_i^2}} \quad \quad \text{Equation 2}$$

As another particular example, the candidate pharmaceutical molecule and a pharmaceutical target may be compared based on a largest common string (LCS) value given by Equation 3 below.

Largest Common String $$NLCS(S_1, S_2) = \frac{\text{length }(LCS(S_1, S_2))^2}{\text{length }(S_1) \times \text{length }(S_2)} \quad \quad \text{Equation 3}$$

As another particular example, the candidate pharmaceutical molecule and a pharmaceutical target may be compared based on a log S value by utilizing regression. A regression model may be built using Delaney data. A linear system may be utilized to solve the logS equation given by Equation 4 below.

log $S = \beta_0 + \beta_1 * \log P + \beta_2 * \text{MolWt} + \beta_3 * \text{NRotatablebond} + \beta_4 * \text{AromaticityProp}$    Equation 4— Log S Equation As another particular example, the candidate pharmaceutical molecule and a pharmaceutical target may be compared based on a half maximal inhibitory concentration (IC50) value (also referred to as a half lifecycle of drug using kinase inhibitor binding affinity using energetic parameter) given by Equation 5 below.

$IC50 = \beta_0 + \beta_1*NHA + \beta_2*IE + \beta_3*vsW + \beta_4*\text{Elect} + \beta_5*\text{H-Bonds} + \beta_6*\text{Solv} + \beta_7*\text{Entropy} + \beta_8*\text{H-Bonds(water-mediated)} + \beta_9*\log P$    Equation 5—IC50 Equation As another particular example, the candidate pharmaceutical molecule and a pharmaceutical target may be compared based on a log D value given by Equation 6 below.

LogD Equation $$\log_{oct/wat} D = \log\left(\sum_{I=0}^{M} f^I p_{oct/wat}^I\right) \quad \quad \text{Equation 6}$$

As other non-limiting examples, the candidate pharmaceutical molecule and a pharmaceutical target may be compared based on LEMONS-based similarity, GRAPE similarity, a Delaney dataset similarity, an EC50 similarity, an H-bond similarity, an aromaticity similarity, a number of rings, a SMILES-based similarity, or the like. Additionally or alternatively, the candidate pharmaceutical molecule and the pharmaceutical target may be compared based on quantitative structure activity relationship (QSAR) models, such as those based on Tanimoto coefficients, cosine similarities, fingerprinting using MinHashed Atom-Paired (MAP) fingerprints, scaffolds, LEMONS, GRAPE, or the like, ligand-based fingerprinting, such as dictionary-based fingerprints, topological-based or path-based fingerprints, circular fingerprints, pharmacophores, or the like, a voting method score, an average score, a large-scale sparse matrix clustering for search, hash maps, or a combination thereof.

The access layer 250 may be configured to support one or more APIs for enabling interaction between the AI/ML engine 240 (or other components of the system 200) and the other devices 270 and/or user devices. The access layer 250 may include one or more generated model APIs 252 and one or more other APIs 254. The generated model APIs 252 may enable interaction between the ML models maintained by the AI/ML engine 240, such as the clustering ML models 242, the ranking ML models 244, or a combination thereof, with the other devices 270. The other APIs 254 may enable interaction between other components of the system 200 and external devices, such as user devices. The API management layer 260 may be configured to manage operation of the APIs supported by the access layer 250 (e.g., the generated model APIs 252 and the other APIs 254).

The other devices 270 may include devices that interact with the system 200 (e.g., the drug screening platform), such as client devices, servers, and the like. For example, the other devices 270 may include a front end client 272, a front end server 274, and a back end server 276. The front end client 272 may be configured to enable client interaction with the ML models maintained by the AI/ML engine 240 to enable pharmaceutical molecule screening and/or ranking at the front end client 272. In some other implementations, the AI/ML engine 240 may train the ML models 242 and/or 244 and provide configuration information associated with the ML models 242 and/or 244 to the front end client 272 such that the front end client 272 stores and operates the ML models 242 and/or 244 to perform pharmaceutical molecule screening and/or ranking. The front end server 274 and the back end server 276 may store data used to support the AI/ML engine 240 (or other components of the system 200), such as training data, processed binding data, results data, input data, and the like.

The message orchestration and logging layer 280 may be configured to generate and transmit messages, such as to user devices, and to log the messages. For example, the message orchestration and logging layer 280 may be configure to transmit messages and/or to initiate display of GUIs that enable user interaction with the molecule screening and/or ranking process, such as providing user input indicating target diseases, target candidate pharmaceutical molecules, target drug properties, and the like, or viewing information regarding the subset of identified pharmaceutical targets, such as names, molecular structures, molecular shapes, or rankings of the subset of pharmaceutical targets based on input information. In some implementations, the message orchestration and logging layer 280 may provide a single point of access for users of the system 200.

As described above, the system 200 supports training of ML models (e.g., the clustering ML models 242, the ranking ML models 244, or a combination thereof) to automatically screen pharmaceutical molecules against pharmaceutical targets and/or rank selected pharmaceutical targets (or combinations of the selected pharmaceutical targets and candidate pharmaceutical molecules). Using artificial intelligence and machine learning to screen the pharmaceutical molecules based on the binding data from the data sources 202 may result in identification of new (e.g., previously-unidentified) uses for existing pharmaceutical molecules and/or uses for newly-identified pharmaceutical molecules.

Figure 3:
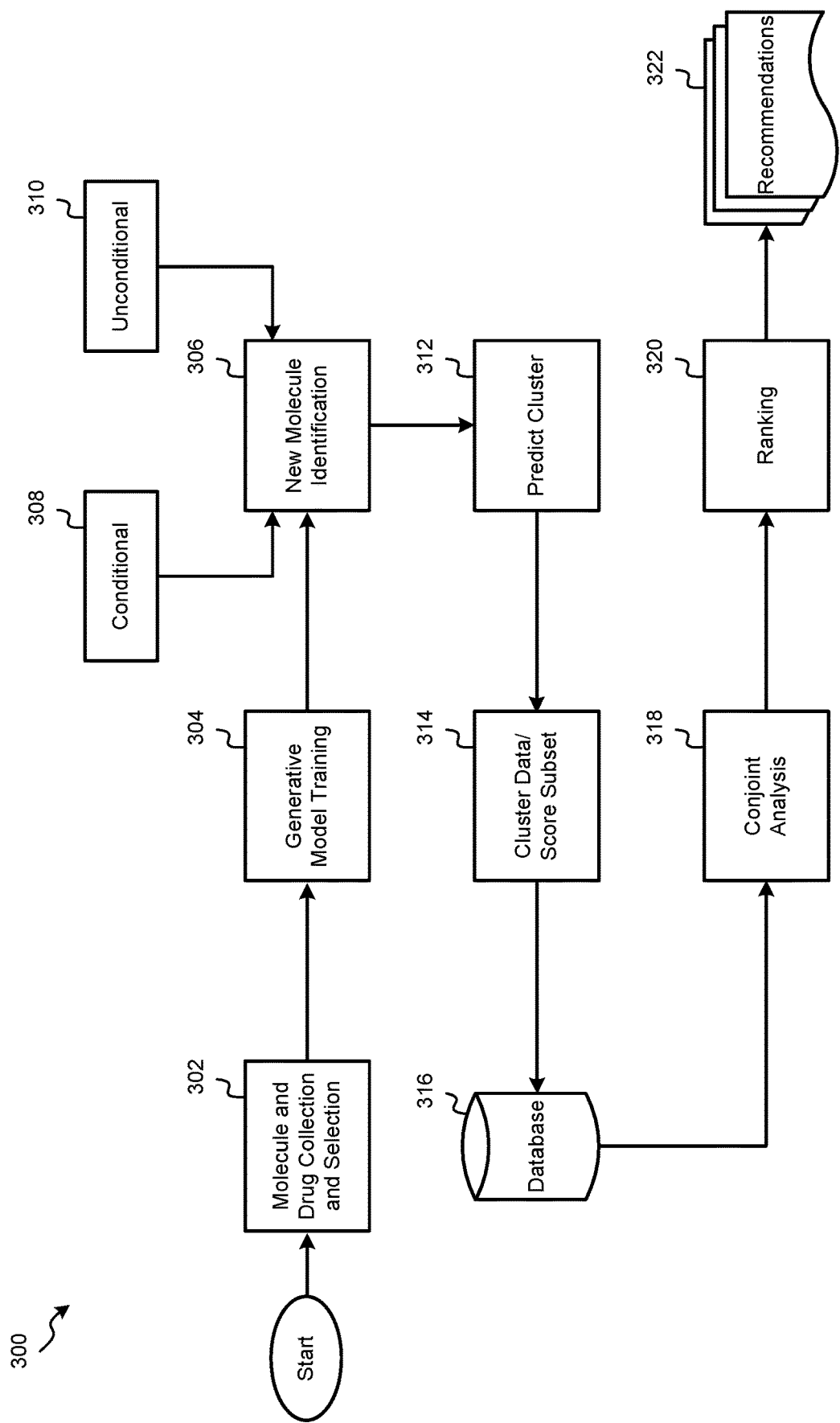
FIG. 3 is a flow diagram illustrating an example of a method for identifying pharmaceutical molecules, screening pharmaceutical molecules, and ranking screened pharmaceutical molecules according to one or more aspects.

Referring to FIG. 3, a flow diagram of an example of a method for identifying pharmaceutical molecules, screening pharmaceutical molecules, and ranking screened pharmaceutical molecules according to one or more aspects is shown as a method 300. In some implementations, the operations of the method 300 may be stored as instructions that, when executed by one or more processors (e.g., the one or more processors of a computing device or a server), cause the one or more processors to perform the operations of the method 300. In some implementations, the method 300 may be performed by one or more components of a system configured to perform pharmaceutical molecule identification (e.g., drug discovery) and/or pharmaceutical molecule screening and ranking, such as one or more components of the system 100 of FIG. 1, one or more components of the system 200 of FIG. 2, one or more components of a system configured to identify pharmaceutical molecules and/or uses for pharmaceutical molecules (e.g., to screen and rank pharmaceutical molecules), or a combination thereof.

The method 300 includes collecting and selecting molecule and drug data, at 302. For example, the system may obtain pharmaceutical data from one or more databases or data sources, such as the ZINC database, the chEMBL database, and the PubChem database, as non-limiting examples. The system may obtain binding data from one or more binding databases, such as the BindingDB database, the DrugBank database, the Therapeutic Targets Database, and the SIDERS as non-limiting examples. Additionally, the system may obtain the Delaney dataset (e.g., a standard regression dataset containing structures and water solubility data for multiple compounds), other types of drug or drug-protein relation data, or a combination thereof. As described above with reference to FIGS. 1-2, the binding data may describe chemical or physical properties of one or more proteins, nucleic acids, cells, etc., that are associated with treating disease states or other conditions.

The method 300 includes training one or more generative ML models, at 304. For example, the system may train one or more generative ML models, such as variational autoencoders (VAEs) or generative adversarial networks (GANs), to identify "new" (e.g., previously-unidentified) pharmaceutical molecules. To illustrate, the generative ML models may be trained using training data that is based on pharmaceutical data that indicates physiochemical structures, efficacy, side effects, solubility, toxicity, and the like, for multiple previously-identified pharmaceutical molecules. In some implementations, the generative ML models may be configured to perform language generation, where the language is a string-based representation of properties indicated by the pharmaceutical data, and newly-identified molecules are identified by generating strings having previously-unidentified combinations of properties, based on the underlying relationships of properties in previously-identified pharmaceutical molecules learned from the pharmaceutical data.

The method 300 includes identifying one or more previously-unidentified molecules, at 306. For example, the system may access the trained generative ML models to identify pharmaceutical molecules that are not previously-identified based on the obtained pharmaceutical data. In some implementations, identifying the new pharmaceutical molecules may include conditional identification of molecules, at 308. For example, the generative ML models may be trained to identify particular types of molecules, such as molecules having (or expected to have) selected properties or molecules that are to be used to cure or treat particular diseases or conditions, as non-limiting examples. Additionally or alternatively, identifying the new pharmaceutical molecules may include unconditional identification of molecules, at 310. For example, the generative ML models may be trained to identify new pharmaceutical molecules without any constraints, instead based only on the underlying similarities between the previously-identified molecules that are derived from the training data.

The method 300 includes predicting a cluster to which one or more pharmaceutical molecules are assigned, at 312. Each of the clusters may include as members multiple pharmaceutical targets, such as proteins or nucleic acids, having similar chemical or physical properties. The pharmaceutical targets may be associated with treating particular disease states or conditions, and if a candidate pharmaceutical molecule is likely to bond with the pharmaceutical targets, the candidate molecule may likely be used to form a drug to treat the particular disease states or conditions. To illustrate, the system may train one or more ML models to perform unsupervised learning to cluster pharmaceutical targets into clusters corresponding to similar chemical or physical properties based on training data generated from the obtained binding data, as described above with reference to FIGS. 1-2. Input data indicating one or more candidate pharmaceutical molecules (e.g., feature vectors generated from strings that combine various structural or other properties of the candidate pharmaceutical molecules) may be provided to the trained ML models to predict the cluster assignment using SSC. Clustering molecules in this manner may be referred to as limiting the search space for diseases to be treated by the candidate pharmaceutical molecules, which may be desirable due to the large chemical search space, which may be on the order of $10^{60}$ molecules. In some implementations, the clustering may include density-based spatial clustering of applications with noise (DBSCAN), K-means clustering, K-means for large-scale clustering (LSC-K), longest common subsequence (LCS) clustering, longest common cyclic subsequence (LCCS) clustering, or the like, in order to cluster large volumes of high dimensional data. In some implementations, newly-identified molecules from the generative ML models may be used as input data to the ML models that perform the clustering to predict the clusters assigned to the newly-identified molecules. Additionally or alternatively, previously-identified molecules (e.g., existing pharmaceutical molecules) may be used as input data to the ML models that perform the clustering to predict other possible uses for the previously-identified pharmaceutical molecules (e.g., a drug that treats diabetes may be determined, after screening/searching, to also treat cancer). Thus, the cluster assignments may identify potential diseases to be treated by newly-identified pharmaceutical molecules as well as additional diseases that may be treated by existing drugs.

The method 300 includes generating cluster data, at 314. The cluster data may indicate the members of each cluster (e.g., the pharmaceutical targets), disease states or conditions associated with the pharmaceutical targets, closest molecules to the cluster for target identification, or a combination thereof. Alternatively, the cluster data may indicate only the members of particular clusters (e.g., the clusters to which the input pharmaceutical molecules are assigned). Additionally or alternatively, the system may determine scores for each pharmaceutical target in a cluster to which a candidate pharmaceutical molecule is assigned, the scores may be used to filter the pharmaceutical targets of the cluster into a subset of pharmaceutical targets (e.g., high-scored pharmaceutical targets), and the cluster data may indicate the scores, the subset of pharmaceutical targets, disease states or conditions associated with the subset of pharmaceutical targets, a ranked list of the subset of pharmaceutical targets, or a combination thereof, as described above with reference to FIGS. 1-2.

The method 300 includes storing the cluster data in a database, at 316. The cluster data may include data representing members of all the clusters, members of particular clusters to which candidate pharmaceutical targets are assigned, disease states or conditions associated with the pharmaceutical targets, scores associated with members of the clusters (e.g., pharmaceutical targets), subsets of pharmaceutical targets associated with scores that satisfy one or more thresholds, ranked lists of subsets of pharmaceutical targets, other cluster data, or the combination thereof. The cluster data may be stored for use in ranking, for use in assigning additional input candidate pharmaceutical molecules to the existing clusters, or a combination thereof.

The method 300 includes performing conjoint analysis on the subset of pharmaceutical targets, at 318. The conjoint analysis may indicate which properties or characteristics of drugs or other pharmaceuticals are most sought after by one or more clients, such as pharmaceutical companies, universities, private research firms, and the like. To illustrate, the conjoint analysis may include providing users with multiple questions that prompt the user to choose between potential drugs having combinations of different properties (as opposed to simply prompting the user to choose desired properties), and analyzing user input to the questions to calculate preference scores for the properties. Although described as being based on user input, in some other implementations, the conjoint analysis may be performed based on extracted or other data mined information, such as from company press releases indicating new drugs or areas of research, market valuations of particular drugs or potential drugs for curing particular diseases, other information, or the like. In some implementations, one or more ML models may be trained to predict preference rankings for input drugs (e.g., combinations of candidate pharmaceutical molecules and pharmaceutical targets) based on training data derived from user responses or other historical information associated with existing drugs.

The method 300 includes ranking the subset of pharmaceutical targets based on the conjoint analysis, at 320. For example, based on ranks determined during the conjoint analysis, the subset of pharmaceutical targets (or drugs to be formed based on the combination of a candidate pharmaceutical molecule with each of the subset of pharmaceutical targets) may be ranked and, optionally, further filtered based on one or more thresholds. The method 300 concludes by outputting recommendations for one or more drugs (e.g., combinations of the candidate pharmaceutical molecule and one or more of the subset of pharmaceutical targets) for use in drug testing and production, at 322. Due to the clustering and ranking, the recommended drugs may be more likely to be useful or marketable, and therefore more likely to result in shorter testing/development cycles and increased revenue to the clients. As explained above, these drugs may include new drugs (e.g., drugs formed from newly-identified pharmaceutical molecules) or drugs having new uses (e.g., existing pharmaceutical molecules which have been determined to have potential in treating different disease states or conditions than those for which the existing pharmaceutical molecules were originally intended to remedy).

Figure 4:
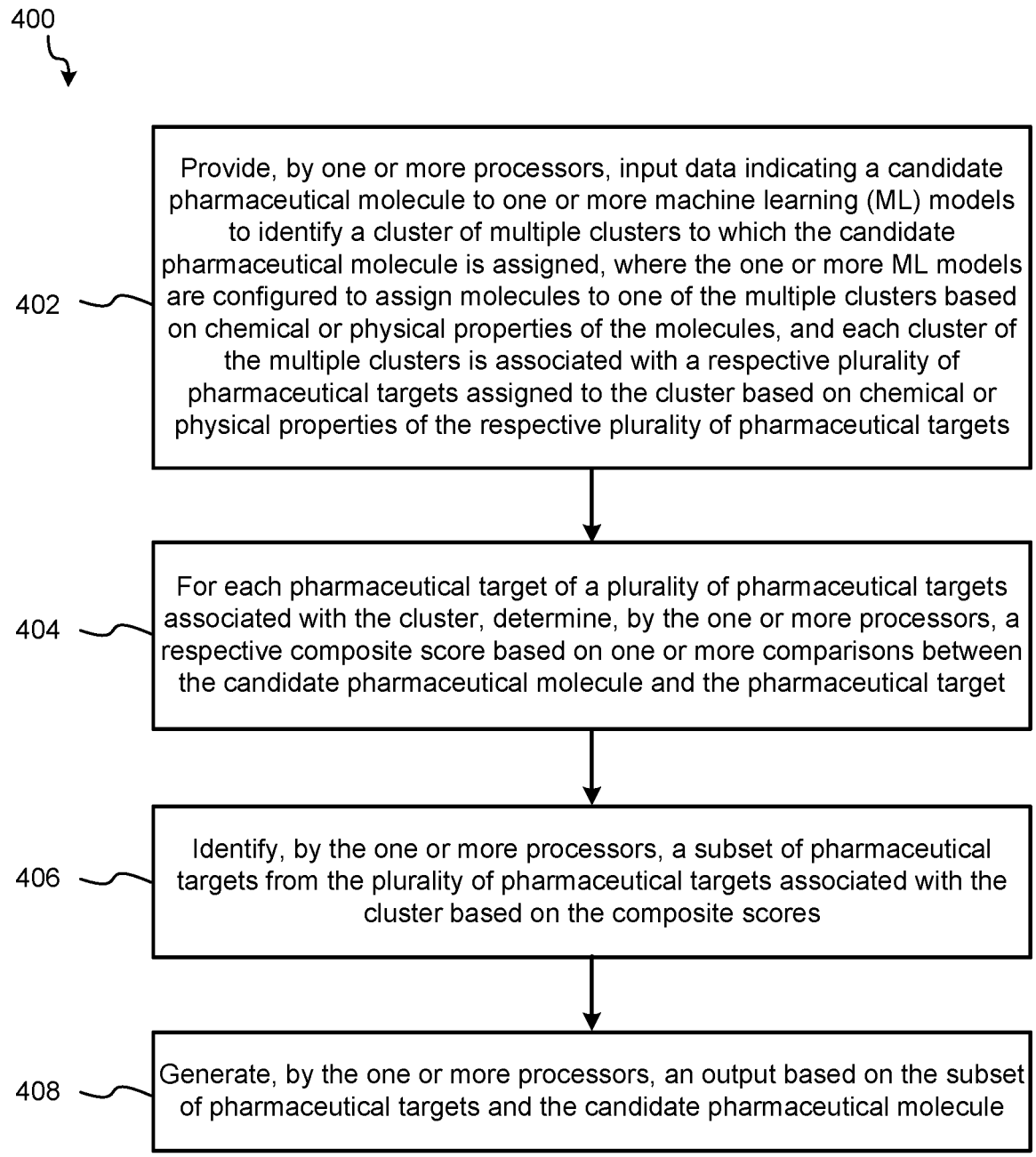
FIG. 4 is a flow diagram illustrating an example of a method for pharmaceutical molecule screening using machine learning according to one or more aspects.

Referring to FIG. 4, a flow diagram of an example of a method for pharmaceutical molecule screening using machine learning according to one or more aspects is shown as a method 400. In some implementations, the operations of the method 400 may be stored as instructions that, when executed by one or more processors (e.g., the one or more processors of a computing device or a server), cause the one or more processors to perform the operations of the method 400. In some implementations, the method 400 may be performed by a computing device, such as the computing device 102 of FIG. 1 (e.g., a computing device configured for pharmaceutical molecule screening or drug discovery), one or more components of the system 200 of FIG. 2, or a combination thereof.

The method 400 includes providing input data indicating a candidate pharmaceutical molecule to one or more ML models to identify a cluster of multiple clusters to which the candidate pharmaceutical molecule is assigned, at 402. The one or more ML models are configured to assign molecules to one of the multiple clusters based on chemical or physical properties of the molecules. Each cluster of the multiple clusters is associated with a respective plurality of pharmaceutical targets assigned to the cluster based on chemical or physical properties of the respective plurality of pharmaceutical targets. For example, the candidate pharmaceutical molecule may be indicated by input data that may include or correspond to the input data 112 of FIG. 1, and the one or more ML models may include or correspond to the ML models 126 of FIG. 1. The method 400 includes, for each pharmaceutical target of a plurality of pharmaceutical targets associated with the cluster, determining a respective composite score based on one or more comparisons between the candidate pharmaceutical molecule and the pharmaceutical target, at 404. For example, the composite scores may include or correspond to the similarity scores 116 of FIG. 1.

The method 400 includes identifying a subset of pharmaceutical targets from the plurality of pharmaceutical targets associated with the cluster based on the composite scores, at 406. For example, the subset of pharmaceutical targets may include or correspond to the subset of pharmaceutical targets 118 of FIG. 1. The method 400 further includes generating an output based on the subset of pharmaceutical targets and the candidate pharmaceutical molecule, at 408. For example, output may include or correspond to the output 144 of FIG. 1.

In some implementations, the method 400 may further include initiating, based on the output, display of a GUI that indicates the candidate pharmaceutical molecule, one or more of the subset of pharmaceutical targets, or a combination thereof. For example, the computing device 102 of FIG. 1 may provide the output 144 to the display device 140 to cause display of a GUI that indicates the input data 112 (e.g., the candidate pharmaceutical molecule), one or more of the subset of pharmaceutical targets 118, or a combination thereof. Additionally or alternatively, generating the output may include transmitting an instruction to an automated or semi-automated system to cause the automated or semi-automated system to initiate development of a sample of a drug that includes the candidate pharmaceutical molecule and at least one of the subset of pharmaceutical targets. For example, the computing device 102 of FIG. 1 may provide the output 144 to the drug production system 162 to initiate formation of one or more drugs from the candidate pharmaceutical molecule and one or more pharmaceutical targets. Additionally or alternatively, the pharmaceutical targets may include proteins, nucleic acids, or a combination thereof.

In some implementations, the one or more ML models may be configured to perform sparse subspace clustering to assign molecules to one of the multiple clusters based on chemical or physical properties of the molecules. For example, the ML models 126 may be configured to perform SSC to assign candidate pharmaceutical molecules to clusters based on chemical or physical properties of the candidate pharmaceutical molecules. Additionally or alternatively, identifying the subset of pharmaceutical targets may include comparing the composite scores with the plurality of pharmaceutical targets associated with the cluster to one or more thresholds and identifying the subset of pharmaceutical targets associated with composite scores that satisfy the one or more thresholds. For example, the subset of pharmaceutical targets 118 may be identified by comparing the similarity scores 116 to one or more thresholds. Additionally or alternatively, the method 400 may also include obtaining binding data indicating the chemical or physical properties of the pharmaceutical targets from one or more databases, generating training data based on features of the binding data, and providing the training data to the one or more ML models to train the one or more ML models to group the pharmaceutical targets into the multiple clusters based on the chemical or physical properties of the pharmaceutical targets. For example, the binding data may include or correspond to the binding data 142 of FIG. 1, and the training data may include or correspond to the training data 110 of FIG. 1. In some such implementations, the method 400 may further include performing NLP on at least a portion of the binding data to convert the at least a portion of the binding data to the training data. For example, the data processing and transformation engine 122 of FIG. 1 may perform NLP on the binding data 142 to generate at least a portion of the training data 110.

In some implementations, the method 400 may include ranking the subset of pharmaceutical targets based on target drug property data. The output includes indication of the ranking of the subset of pharmaceutical targets. For example, the ranking engine 132 of FIG. 1 may rank the subset of pharmaceutical targets 118 based on the target drug property data 146. In some such implementations, ranking the subset of pharmaceutical targets may include performing conjoint analysis on the candidate pharmaceutical molecule, the subset of pharmaceutical targets, and the target drug property data. For example, the ranking engine 132 of FIG. 1 may perform conjoint analysis on the input data 112 (which indicates the candidate pharmaceutical molecule), the subset of pharmaceutical targets 118, and the target drug property data 146. In some such implementations, ranking the subset of pharmaceutical targets may include providing input data indicating the candidate pharmaceutical molecule and the subset of pharmaceutical targets to a second set of one or more ML models to rank the subset of pharmaceutical targets, and the second set of one or more ML models may be configured to rank combinations of molecules and pharmaceutical targets based on similarities of the combinations to one or more drugs indicated by the target drug property data. For example, the second set of one or more ML models may include or correspond to the ML models 134 of FIG. 1. In some such implementations, the method 400 may further include obtaining the target drug property data and generating second training data based on the target drug property data to train the second set of one or more ML models to rank input combinations based on similarities of the input combinations to the one or more drugs. For example, the computing device 102 of FIG. 1 may obtain the target drug property data 146, such as from the client device 160, and use the target drug property data 146 to generate training data for the ML models 134. In some such implementations, obtaining the target drug property data may include providing survey documents to one or more other devices and receiving response data based on the survey documents, extracting the target drug property data from pharmaceutical news data, market research, pharmaceutical press releases, or a combination thereof, receiving user input indicating the target drug property data, or a combination thereof.

In some implementations, the candidate pharmaceutical molecule may include a previously-identified pharmaceutical molecule that is indicated by pharmaceutical data obtained from one or more databases. For example, the candidate pharmaceutical molecule indicated by the input data 112 of FIG. 1 may be indicated by pharmaceutical data obtained from the ZINC database, the chEMBL database, or the PubChem database, as non-limiting examples. Additionally or alternatively, the candidate pharmaceutical molecule may be identified based on one or more generative ML models configured to identify pharmaceutical molecules based on previously-identified pharmaceutical molecules. For example, the candidate pharmaceutical molecule indicated by the input data 112 of FIG. 1 may be identified using one or more generative ML models, as further described above with reference to FIG. 3.

In some implementations, the composite score associated with a pharmaceutical target of the plurality of pharmaceutical targets may include an average score based on a plurality of similarity measurements between molecular fingerprints associated with the candidate pharmaceutical molecule and the pharmaceutical target. For example, the similarity scores 116 of FIG. 1 may include composite scores that are generated based on a plurality of similarity measurements between molecular fingerprints associated with the candidate pharmaceutical molecule indicated by the input data 112 and molecular fingerprints associated with the subset of pharmaceutical targets 118. In some such implementations, the plurality of similarity measurements may include a Tanimoto coefficient, a cosine similarity, a LCS similarity, a LEMONS-based similarity, a GRAPE similarity, a log S similarity, a Delaney dataset similarity, an IC50 similarity, an EC50 similarity, a log D similarity, an H-bond similarity, an aromaticity similarity, a SMILES-based similarity, or combination thereof, as further described above with reference to FIG. 2.

It is noted that other types of devices and functionality may be provided according to aspects of the present disclosure and discussion of specific devices and functionality herein have been provided for purposes of illustration, rather than by way of limitation. It is noted that the operations of the method 300 of FIG. 3 and the method 400 of FIG. 4 may be performed in any order, or that operations of one method may be performed during performance of another method, such as the method 400 of FIG. 4 including one or more operations of the method 300 of FIG. 3. It is also noted that the method 300 of FIG. 3 and the method 400 of FIG. 4 may also include other functionality or operations consistent with the description of the operations of the system 100 of FIG. 1 and/or the system 200 of FIG. 2.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The functional blocks and modules described herein (e.g., the functional blocks and modules in FIGS. 1-4) may comprise processors, electronics devices, hardware devices, electronics components, logical circuits, memories, software codes, firmware codes, etc., or any combination thereof. In addition, features discussed herein relating to FIGS. 1-4 may be implemented via specialized processor circuitry, via executable instructions, and/or combinations thereof.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified—and includes what is specified; e.g., substantially 90 degrees includes 90 degrees and substantially parallel includes parallel—as understood by a person of ordinary skill in the art. In any disclosed aspect, the term "substantially" may be substituted with "within [a percentage] of" what is specified, where the percentage includes 0.1, 1, 5, and 10 percent; and the term "approximately" may be substituted with "within 10 percent of" what is specified. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or. Additionally, the phrase "A, B, C, or a combination thereof" or "A, B, C, or any combination thereof" includes: A alone, B alone, C alone, a combination of A and B, a combination of A and C, a combination of B and C, or a combination of A, B, and C.

The terms "comprise" and any form thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any implementation of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. Aspects of one example may be applied to other examples, even though not described or illustrated, unless expressly prohibited by this disclosure or the nature of a particular example.

Those of skill would further appreciate that the various illustrative logical blocks, modules, circuits, and algorithm steps (e.g., the logical blocks in FIGS. 1-4) described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Skilled artisans will also readily recognize that the order or combination of components, methods, or interactions that are described herein are merely examples and that the components, methods, or interactions of the various aspects of the present disclosure may be combined or performed in ways other than those illustrated and described herein.

The various illustrative logical blocks, modules, and circuits described in connection with the disclosure herein may be implemented or performed with a general-purpose processor, a digital signal processor (DSP), an ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be implemented directly in hardware, in a software module executed by a processor, or in a combination of the two. A software module may reside in RAM memory, flash memory, ROM memory, EPROM memory, EEPROM memory, registers, hard disk, a removable disk, a CDROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. Computer-readable storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, a connection may be properly termed a computer-readable medium. For example, if the software is transmitted from a website, server, or other remote source using a coaxial cable, fiber optic cable, twisted pair, or digital subscriber line (DSL), then the coaxial cable, fiber optic cable, twisted pair, or DSL, are included in the definition of medium. Disk and disc, as used herein, includes compact disc (CD), laser disc, optical disc, digital versatile disc (DVD), hard disk, solid state disk, and blu-ray disc where disks usually reproduce data magnetically, while discs reproduce data optically with lasers. Combinations of the above should also be included within the scope of computer-readable media.

The above specification and examples provide a complete description of the structure and use of illustrative implementations. Although certain examples have been described above with a certain degree of particularity, or with reference to one or more individual examples, those skilled in the art could make numerous alterations to the disclosed implementations without departing from the scope of this disclosure. As such, the various illustrative implementations of the methods and systems are not intended to be limited to the particular forms disclosed. Rather, they include all modifications and alternatives falling within the scope of the claims, and examples other than the one shown may include some or all of the features of the depicted example. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one aspect or may relate to several implementations.

The claims are not intended to include, and should not be interpreted to include, means plus- or step-plus-function limitations, unless such a limitation is explicitly recited in a given claim using the phrase(s) "means for" or "step for," respectively.

Although the aspects of the present disclosure and their advantages have been described in detail, it should be understood that various changes, substitutions and alterations can be made herein without departing from the spirit of the disclosure as defined by the appended claims. Moreover, the scope of the present application is not intended to be limited to the particular implementations of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding aspects described herein may be utilized according to the present disclosure. Accordingly, the appended claims are intended to include within their scope such processes, machines, manufacture, compositions of matter, means, methods, or steps.

What is claimed is:

1. A method for pharmaceutical molecule screening using machine learning, the method comprising:
providing, by one or more processors, input data indicating a candidate pharmaceutical molecule to one or more machine learning (ML) models to identify a cluster of multiple clusters to which the candidate pharmaceutical molecule is assigned,
wherein the one or more ML models are configured to assign molecules to one of the multiple clusters based on chemical or physical properties of the molecules, and
wherein each cluster of the multiple clusters is associated with a respective plurality of pharmaceutical targets assigned to the cluster based on chemical or physical properties of the respective plurality of pharmaceutical targets;
for each pharmaceutical target of a plurality of pharmaceutical targets associated with the cluster:
performing, by the one or more processors, one or more comparisons between a molecular fingerprint associated with the pharmaceutical target and a molecular fingerprint associated with the candidate pharmaceutical molecule to generate one or more similarity values; and
determining, by the one or more processors, a respective composite score based on the one or more similarity values;
identifying, by the one or more processors, a subset of pharmaceutical targets from the plurality of pharmaceutical targets associated with the cluster,
wherein the subset of pharmaceutical targets is associated with composite scores that satisfy a threshold; and
generating, by the one or more processors, an output based on the subset of pharmaceutical targets and the candidate pharmaceutical molecule,
wherein generating the output comprises transmitting an instruction to an automated or semi-automated system to cause the automated or semi-automated system to initiate development of a sample of a pharmaceutical product that includes the candidate pharmaceutical molecule and at least one of the subset of pharmaceutical targets.

2. The method of claim 1, further comprising initiating, by the one or more processors and based on the output, display of a graphical user interface (GUI) that indicates the candidate pharmaceutical molecule, one or more of the subset of pharmaceutical targets, or a combination thereof.

3. The method of claim 1, wherein the pharmaceutical targets comprise proteins, nucleic acids, or a combination thereof.

4. The method of claim 1, wherein the one or more ML models are configured to perform sparse subspace clustering to assign molecules to one of the multiple clusters based on chemical or physical properties of the molecules.

5. The method of claim 1, wherein identifying the subset of pharmaceutical targets comprises:
comparing, by the one or more processors, the composite scores associated with the plurality of pharmaceutical targets to to the threshold to identify the subset of pharmaceutical targets associated with composite scores that satisfy the threshold.

6. The method of claim 1, further comprising:
obtaining, by one or more processors, binding data indicating the chemical or physical properties of the pharmaceutical targets from one or more databases;
generating, by the one or more processors, training data based on features of the binding data; and
providing, by the one or more processors, the training data to the one or more ML models to train the one or more ML models to group the pharmaceutical targets into the multiple clusters based on the chemical or physical properties of the pharmaceutical targets.

7. The method of claim 6, further comprising performing, by the one or more processors, natural language processing (NLP) on at least a portion of the binding data to convert the at least a portion of the binding data to the training data.

8. The method of claim 1, further comprising ranking, by the one or more processors, the subset of pharmaceutical targets based on target drug property data,
wherein the output includes indication of the ranking of the subset of pharmaceutical targets.

9. The method of claim 8, wherein ranking the subset of pharmaceutical targets comprises performing, by the one or more processors, conjoint analysis on the candidate pharmaceutical molecule, the subset of pharmaceutical targets, and the target drug property data.

10. The method of claim 9, wherein ranking the subset of pharmaceutical targets comprises providing, by the one or more processors, input data indicating the candidate pharmaceutical molecule and the subset of pharmaceutical targets to a second set of one or more ML models to rank the subset of pharmaceutical targets,
wherein the second set of one or more ML models is configured to rank combinations of molecules and pharmaceutical targets based on similarities of the combinations to one or more drugs indicated by the target drug property data.

11. The method of claim 10, further comprising:
obtaining, by the one or more processors, the target drug property data; and
generating, by the one or more processors, second training data based on the target drug property data to train the second set of one or more ML models to rank input combinations based on similarities of the input combinations to the one or more drugs.

12. The method of claim 11, wherein obtaining the target drug property data comprises:
providing, by the one or more processors, survey documents to one or more other devices and receiving response data based on the survey documents,
extracting, by the one or more processors, the target drug property data from pharmaceutical news data, market research, pharmaceutical press releases, or a combination thereof,
receiving, by the one or more processors, user input indicating the target drug property data, or
a combination thereof.

13. The method of claim 1, wherein the one or more comparisons are performed based on one or more similarity metrics, and wherein determining the respective composite score comprises determining an average or a weighted average of the one or more similarity values.

14. A system for pharmaceutical molecule screening using machine learning, the system comprising:
a memory; and
one or more processors communicatively coupled to the memory, the one or more processors configured to:
provide input data indicating a candidate pharmaceutical molecule to one or more machine learning (ML) models to identify a duster of multiple clusters to which the candidate pharmaceutical molecule is assigned,
wherein the one or more ML models are configured to assign molecules to one of the multiple clusters based on chemical or physical properties of the molecules, and
wherein each cluster of the multiple clusters is associated with a respective plurality of pharmaceutical targets assigned to the cluster based on chemical or physical properties of the respective plurality of pharmaceutical targets;
for each pharmaceutical target of a plurality of pharmaceutical targets associated with the cluster:
perform one or more comparisons between a molecular fingerprint associated with the pharmaceutical target and a molecular fingerprint associated with the candidate pharmaceutical molecule to generate one or more similarity values; and
determine a respective composite score based on the one or more similarity values;
identify a subset of pharmaceutical targets from the plurality of pharmaceutical targets associated with the cluster,
wherein the subset of pharmaceutical targets is associated with composite scores that satisfy a threshold; and
generate an output based on the subset of pharmaceutical targets and the candidate pharmaceutical molecule,
wherein generating the output comprises transmitting an instruction to an automated or semi-automated system to cause the automated or semi-automated system to initiate development of a sample of a drug that includes the candidate pharmaceutical molecule and at least one of the subset of pharmaceutical targets.

15. The system of claim 14, wherein the candidate pharmaceutical molecule comprises a previously-identified pharmaceutical molecule that is indicated by pharmaceutical data obtained from one or more databases.

16. The system of claim 14, wherein the candidate pharmaceutical molecule is identified based on one or more generative ML models configured to identify pharmaceutical molecules based on previously-identified pharmaceutical molecules.

17. The system of claim 14, further comprising one or more interfaces configured to enable communication with one or more databases, a display device, a client device, a drug production system, or a combination thereof,
wherein the one or more databases are configured to store binding data indicating the chemical or physical properties of the pharmaceutical targets.

18. A non-transitory computer-readable storage medium storing instructions that, when executed by one or more processors, cause the one or more processors to perform operations for pharmaceutical molecule screening using machine learning, the operations comprising:
providing input data indicating a candidate pharmaceutical molecule to one or more machine learning (ML) models to identify a cluster of multiple clusters to which the candidate pharmaceutical molecule is assigned,
wherein the one or more ML models are configured to assign molecules to one of the multiple clusters based on chemical or physical properties of the molecules, and
wherein each cluster of the multiple clusters is associated with a respective plurality of pharmaceutical targets assigned to the cluster based on chemical or physical properties of the respective plurality of pharmaceutical targets;
for each pharmaceutical target of a plurality of pharmaceutical targets associated with the cluster:
performing one or more comparisons between a molecular fingerprint associated with the pharmaceutical target and a molecular fingerprint associated with the candidate pharmaceutical molecule to generate one or more similarity values; and
determining a respective composite score based on the one or more between the candidate pharmaceutical molecule and the pharmaceutical target similarity values;
identifying a subset of pharmaceutical targets from the plurality of pharmaceutical targets associated with the cluster,
wherein the subset of pharmaceutical targets is associated with composite scores that satisfy a threshold; and
generating an output based on the subset of pharmaceutical targets and the candidate pharmaceutical molecule,
wherein generating the output comprises transmitting an instruction to an automated or semi-automated system to cause the automated or semi-automated system to initiate development of a sample of a drug that includes the candidate pharmaceutical molecule and at least one of the subset of pharmaceutical targets.

19. The non-transitory computer-readable storage medium of claim 18, wherein the composite score associated with a pharmaceutical target of the plurality of pharmaceutical targets comprises an average score based on a plurality of similarity values determined for the candidate pharmaceutical molecule.

20. The non-transitory compute readable storage medium of claim 19, wherein the plurality of similarity values comprises a Tanimoto coefficient, a cosine similarity, a largest common string (LCS) similarity, a Library for the Enumeration of Modular Natural Structures (LEMONS)-based similarity, a retrobiosynthesis and alignment (GRAPE) similarity, an intrinsic solubility (Log S) similarity, a Delaney dataset similarity, a half maximal inhibitory concentration (IC50) similarity, a half maximal effective concentration (EC50) similarity, a partition between lipid and aqueous phases (log D) similarity, a hydrogen bond (H-bond) similarity, an aromaticity similarity, a simplified molecular-input line-entry system (SMILES)-based similarity, or combination thereof.

* * * * *

UNITED STATES PATENT AND TRADEMARK OFFICE
CERTIFICATE OF CORRECTION

PATENT NO. : 11,127,488 B1
APPLICATION NO. : 17/155021
DATED : September 21, 2021
INVENTOR(S) : Dhruv Bajpai et al.

Page 1 of 1

It is certified that error appears in the above-identified patent and that said Letters Patent is hereby corrected as shown below:

In the Claims

At Column 39, Claim number 14, Line number 8, delete "duster" and replace with --cluster--.
At Column 40, Claim number 18, starting at Line number 24, delete "determining a respective composite score based on the one or more between the candidate pharmaceutical molecule and the pharmaceutical target similarity values" and replace with --determining a respective composite score based on the one or more similarity values--.
At Column 40, Claim number 20, Line number 49, delete "compute readable" and replace with --computer-readable--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*